US007445898B2

(12) United States Patent
Li et al.

(10) Patent No.: US 7,445,898 B2
(45) Date of Patent: Nov. 4, 2008

(54) QUANTITATIVE AMPLIFICATION WITH A LABELED PROBE AND 3' TO 5' EXONUCLEASE ACTIVITY

(75) Inventors: Bin Li, San Mateo, CA (US); Lei Xi, Foster City, CA (US); Yan Wang, San Francisco, CA (US); Peter B. Vander Horn, Foster City, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 0 days.

(21) Appl. No.: 11/097,463

(22) Filed: Mar. 31, 2005

(65) Prior Publication Data

US 2006/0024695 A1   Feb. 2, 2006

Related U.S. Application Data

(60) Provisional application No. 60/559,137, filed on Apr. 1, 2004.

(51) Int. Cl.
*C12Q 1/68* (2006.01)
*C12P 19/34* (2006.01)

(52) U.S. Cl. .......................................... 435/6; 435/91.2
(58) Field of Classification Search ....................... None
See application file for complete search history.

(56) References Cited

U.S. PATENT DOCUMENTS

| | | | |
|---|---|---|---|
| 4,851,331 A | 7/1989 | Vary et al. | |
| 5,210,015 A | 5/1993 | Gelfand et al. | |
| 5,391,480 A * | 2/1995 | Davis et al. ..................... | 435/6 |
| 5,487,972 A | 1/1996 | Gelfand et al. | |
| 5,521,301 A | 5/1996 | Wallace et al. | |
| 5,545,552 A | 8/1996 | Mathur | |
| 5,639,611 A | 6/1997 | Wallace et al. | |
| 5,736,626 A | 4/1998 | Mullah et al. | |
| 5,759,772 A | 6/1998 | Kirkpatrick et al. | |
| 5,801,155 A * | 9/1998 | Kutyavin et al. ............... | 514/44 |
| 5,804,375 A | 9/1998 | Gelfand et al. | |
| 5,848,717 A | 12/1998 | Bosl et al. | |
| 5,851,770 A | 12/1998 | Babon et al. | |
| 5,955,268 A | 9/1999 | Granados et al. | |
| 6,001,567 A | 12/1999 | Brow et al. | |
| 6,120,992 A | 9/2000 | Wagner, Jr. | |
| 6,174,670 B1 | 1/2001 | Wittwer et al. | |
| 6,248,526 B1 | 6/2001 | Weimer | |
| 6,277,578 B1 | 8/2001 | Shultz et al. | |
| 6,355,435 B1 * | 3/2002 | Wilson et al. ................... | 435/6 |
| 6,391,551 B1 | 5/2002 | Shultz et al. | |
| 6,399,320 B1 * | 6/2002 | Markau et al. ................. | 435/15 |
| 6,511,810 B2 | 1/2003 | Bi et al. | |
| 6,511,845 B1 | 1/2003 | Davis et al. | |
| 6,528,254 B1 | 3/2003 | Sorge | |
| 6,610,486 B1 | 8/2003 | Dahlhauser | |
| 6,653,078 B2 | 11/2003 | Lewis et al. | |
| 6,720,148 B1 | 4/2004 | Nikiforov | |
| 2002/0142336 A1 | 10/2002 | Smith et al. | |
| 2003/0036073 A1 | 2/2003 | Saba | |
| 2003/0049657 A1 * | 3/2003 | Cherry ........................... | 435/6 |
| 2003/0119150 A1 | 6/2003 | Ankenbauer et al. | |
| 2003/0138830 A1 * | 7/2003 | Wang et al. ..................... | 435/6 |
| 2003/0165920 A1 | 9/2003 | Chou et al. | |
| 2003/0180741 A1 * | 9/2003 | Hogrefe et al. ................. | 435/6 |
| 2003/0211489 A1 | 11/2003 | Shen et al. | |
| 2003/0228616 A1 * | 12/2003 | Arezi et al. ..................... | 435/6 |
| 2004/0053279 A1 | 3/2004 | Decker et al. | |
| 2005/0026166 A1 * | 2/2005 | Bi ................................... | 435/6 |

FOREIGN PATENT DOCUMENTS

EP          0 070 685 A2      1/1983

OTHER PUBLICATIONS

Proudnikov et al. Optimizing primer-probe design for fluorescent PCR. J. Neuro. Meth. (2003) 123: 31-45.*
Bi, et al., "Detection of known mutation by proof-reading PCR," *Nucleic Acids Research* 26(2): 3073-3075 (1998).
Cardullo et al., "Detection of nucleic acid hybridization by nonradiative fluorescence resonance energy transfer", *Proc. Natl. Acad. Sci.* 85: 8790-8794 (1988).
Chen et al., "Homogeneous genotyping assays for single nucleotide polymorphisms with fluorescence resonance energy transfer detection", *Genetic Analysis: Biomolecular Engineering* 14: 157-163 (1999).
Lu et al., "Methyl-direct4d repair of DNA base-pair mismatches in vitro," *PNAS* 80: 4639-4643 (Aug. 1983).
Newton et al., "Analysis of any point mutation in DNA. The amplification refractory mutation system (ARMS)," *Nucleic Acids Research* 17(7): 2503-2516 (1989).
Pastinen et al., "A system for specific, high-throughput genotyping by allele-specific primer extension of microarrays," *Genome Research* 10: 1031-1042 (2000).
Saiki et al., "Enzymatic Amplification of β-globin Genomic Sequences and Restriction Site Analysis for Diagnosis of Sickle Cell Anemia" *Science* 230: 1350-1354 (1985).
Shumaker et al., "Mutation Detection by Solid Phase Primer Extension", *Human Mutation* 7: 346-354 (1996).
Ugozzoli et al., "Detection of Specific Alleles by Using Allele-Specific Primer Extension Followed by Capture on Solid Support", *GATA* 9:4: 107-112 (1992).
Wang et al., "Large-Scale Identification, Mapping, and Genotyping of Single-Nucleotide Polymorphisms in the Human Genome", *Science* 280: 1077-1082 (1998).
Wittwer et al., "Rapid cycle allele-specific amplification: Studies with the cystic fibrosis ΔF508 Locus," *Clinical Chemistry* 39(5): 804-809 (1993).

* cited by examiner

*Primary Examiner*—Kenneth R. Horlick
*Assistant Examiner*—David C Thomas
(74) *Attorney, Agent, or Firm*—Townsend and Townsend and Crew LLP

(57) ABSTRACT

This invention provides methods and kits for performing a quantitative amplification reaction. The method employs a polymerase enzyme and an enzyme having a 3' to 5' exonuclease activity that cleaves the 3' oligonucleotide of the probe.

41 Claims, 13 Drawing Sheets

1, 95°C 10 min
2, 95°C 15s
3, 60°C 30s
4, read
5, 72°C 30s
8, read
9, go to 2 for 49 times
10, 72°C 10 min

Figure 7

| | |
|---|---|
| GUSB101 | FAM-TGGGCACTGCCAATCCTCAGCT-BHQ1 |
| PGK101 | FAM-AATCTTCACCATTCTTCTCAGCA-BHQ1 |
| TFRC101 | FAM-TGACAAATCTGTCTGTTTTCTCAGCT-BHQ1 |
| RPLP107 | FAM-AGAAGGCCTTGACCTTTTCAGCT-BHQ1 |
| GAPD | Cy5-CAAGCTTCCCGTTCTCAGCT-BHQ2 |

Mismatch to template → (indicating position in GUSB101)

Preferred bases (bracket at right side of sequences)

Figure 10

| | |
|---|---|
| SDHA | Q-GTCATGCAGGCCTGG0GATAAAGTCCCTCTGCAT |
| HMBS | Q-AGCCTCGTACCCTGGCC0GCAGTTTGAATTTTT |
| TBP | Q-CCTGGTGCCACoCCCTGCAACTCTTCCAGGA |
| UBC | Q-GATCTGCATTGTC0AGTGACGATCACAGATCC |
| Rrm | Q-CCACCTTGATCC0CATATCTAGCTGTTGGTGG |

Italic: Mismatches
Nonbold T : internal labelled T
0 : abasic site

SEQUENCE LISTING

<160> NUMBER OF SEQ ID NOS: 35

<210> SEQ ID NO 1
<211> LENGTH: 2274
<212> TYPE: DNA
<213> ORGANISM: Artificial Sequence
<220> FEATURE:
<223> OTHER INFORMATION: Description of Artificial Sequence:hybrid
      enzyme A6 mutant error-correcting polymerase lacking polymerase
      activity retaining 3' to 5' exonuclease activity (pol- exo+)
<220> FEATURE:
<221> NAME/KEY: CDS
<222> LOCATION: (1)..(2274)
<223> OTHER INFORMATION: hybrid enzyme A6

<400> SEQUENCE: 1

```
atgatcctgg atgctgacta catcactgaa gacggcaaac cgattatccg tctgttcaaa      60
aaagagaacg gcgaatttaa ggttgagtat gatcgcaact ttcgtccata catttacgct     120
ctgctgagag atgattctca gattgatgaa gttaaaaaaa tcactgctga gcgccatggc     180
aagattgttc gtatcattga tgcggaaaag gtagaaaaga aatttctggg cagaccaatc     240
accgtgtgga gactgtattt cgaacatcca agatgttc cggctattcg cgataaagtt     300
cgcgaacatc ctgcagttgt tgacatcttc gaatacgata ttccatttgc aaagcgttac     360
ctcatcgaca aaggcctgat accaatggag ggcgaggaag aactcaagct cctggcgttc     420
gatatagaaa ccctctatca cgaaggcgaa gagtttggta aaggcccaat tataatgatc     480
agctatgcag atgaaaacga agcaaaggtg attacttgga aaaaaataga tctcccatac     540
gttgaggtta tcttccga gcgcgagatg attaagcgct ttctcagaat tatccgcgag     600
aaggatccgg acgttatcgt tacttataac ggcgactctt ttgacctccc atatctggtg     660
aaacgcgcag aaaaactcgg tattaaactg cctctcggcc gtgatggttc cgagccgaag     720
atgcagcgtc tcggcgatat gaccgctgta gaagttaagg gtcgtatcca tttcgacctg     780
tatcatgtaa ttactcgtac tattaacctc ccgacttaca ctctcgaggc tgtatatgaa     840
gcaatttttg gtaagccgaa ggagaaggta tacgcccatg agattgcaaa ggcgtgggaa     900
accggtaaga acctcgagcg tgttgcaaaa tactccatgg aagatgcaaa ggcgacttat     960
gaactcggca agaattcttt cccaatggaa gctcagctct ctgcctggt ggccaacca    1020
ctgtgggatg tttctcgttc ttccaccggt aacctcgtag agtggttct cctgcgcaaa    1080
gcgtacgaac gcaacgaagt ggctccgaac aagccatctg aagaagagta tgaacgccgt    1140
ctccgcgagt cttacgctgg tggctttgtt aaagagccag aaaagggcct ctgggaaaac    1200
```

-continued

```
ctcgtgtacc tcgatttcg ctctctgtat ccgtctatta tcattaccca caacgtgtct      1260
ccggatactc tcaaccgcga gggctgcaga gagtatgatg ttgctccgga agtaggccac      1320
aagttctgca aggacttccc gggctttatt ccgtctctcc tgaaacgtct gctcgaggaa      1380
cgccaagaga ttaagactaa aatgaaggcg tcccaggatc cgattgaaaa aataatgctc      1440
gactatcgcc aaagagcgat taaaatcctc gcaaactctt attacggcta ttatggctat      1500
gcaaaagcac gctggtactg taaggagtgt gctgagtccg ttactgcttg gggtcgcgaa      1560
tacatcgagc tcgtgcggaa ggagctcgaa gaaaagtttg gctttaaagt tctctacatt      1620
gacactgatg gtctctatgc gactattccg gtggtgagc ctgaggaaat taagaaaaag       1680
gctctagaat ttgtgaaata cattaactcg aagctcccgg gtctcctgga gctcgaatat      1740 gaaggcttt atgttcgcgg cttcttcgtt accaagaaga gatatgcggt gattgatgaa       1800
gaaggcaaaa ttattactcg tggtctcgag attgtgcgcc gtgattggag cgaaattgcg      1860
aaagaaactc aagctagagt tctcgaggct attctcaaac acggcaacgt tgaagaagct      1920
gtgaaaattg taaagaagt aacccaaaag ctcgctaaat atgaaattcc gccagagaag       1980
ctcgcgattt atgagcagat tactcgcccg ctgcatgagt ataaggcgat tggtccgcac      2040
gtggctgttg caagagact ggctgctaga ggcgtgaaag ttagaccggg tatggtaatt       2100
ggctacattg tactccgcgg cgatggtccg attagcaacc gtgcaattct agctgaggaa      2160
tacgatctga aaaagcacaa gtatgacgca gaatattaca ttgagaacca ggtgctcccg      2220
gcggtactcc gtattctgga ggcttttggc taccgtaagg aagacctccg ctga            2274
```

<210> SEQ ID NO 2
<211> LENGTH: 757
<212> TYPE: PRT
<213> ORGANISM: Artificial Sequence
<220> FEATURE:
<223> OTHER INFORMATION: Description of Artificial Sequence:hybrid
      enzyme A6 mutant error-correcting polymerase lacking polymerase
      activity retaining 3' to 5' exonuclease activity (pol- exo+)

<400> SEQUENCE: 2

```
Met Ile Leu Asp Ala Asp Tyr Ile Thr Glu Asp Gly Lys Pro Ile Ile
  1               5                  10                  15

Arg Leu Phe Lys Lys Glu Asn Gly Glu Phe Lys Val Glu Tyr Asp Arg
             20                  25                  30

Asn Phe Arg Pro Tyr Ile Tyr Ala Leu Leu Arg Asp Asp Ser Gln Ile
         35                  40                  45

Asp Glu Val Lys Lys Ile Thr Ala Glu Arg His Gly Lys Ile Val Arg
     50                  55                  60

Ile Ile Asp Ala Glu Lys Val Glu Lys Lys Phe Leu Gly Arg Pro Ile
 65                  70                  75                  80

Thr Val Trp Arg Leu Tyr Phe Glu His Pro Gln Asp Val Pro Ala Ile
                 85                  90                  95

Arg Asp Lys Val Arg Glu His Pro Ala Val Val Asp Ile Phe Glu Tyr
                100                 105                 110

Asp Ile Pro Phe Ala Lys Arg Tyr Leu Ile Asp Lys Gly Leu Ile Pro
            115                 120                 125

Met Glu Gly Glu Glu Glu Leu Lys Leu Leu Ala Phe Asp Ile Glu Thr
        130                 135                 140

Leu Tyr His Glu Gly Glu Glu Phe Gly Lys Gly Pro Ile Ile Met Ile
145                 150                 155                 160

Ser Tyr Ala Asp Glu Asn Glu Ala Lys Val Ile Thr Trp Lys Lys Ile
```

```
                       165                 170                 175
Asp Leu Pro Tyr Val Glu Val Val Ser Ser Glu Arg Glu Met Ile Lys
            180                 185                 190
Arg Phe Leu Arg Ile Ile Arg Glu Lys Asp Pro Asp Val Ile Val Thr
                195                 200                 205
Tyr Asn Gly Asp Ser Phe Asp Leu Pro Tyr Leu Val Lys Arg Ala Glu
            210                 215                 220
Lys Leu Gly Ile Lys Leu Pro Leu Gly Arg Asp Gly Ser Glu Pro Lys
225                 230                 235                 240
Met Gln Arg Leu Gly Asp Met Thr Ala Val Glu Val Lys Gly Arg Ile
                245                 250                 255
His Phe Asp Leu Tyr His Val Ile Thr Arg Thr Ile Asn Leu Pro Thr
            260                 265                 270
Tyr Thr Leu Glu Ala Val Tyr Glu Ala Ile Phe Gly Lys Pro Lys Glu
        275                 280                 285
Lys Val Tyr Ala His Glu Ile Ala Lys Ala Trp Glu Thr Gly Lys Asn
        290                 295                 300
Leu Glu Arg Val Ala Lys Tyr Ser Met Glu Asp Ala Lys Ala Thr Tyr
305                 310                 315                 320
Glu Leu Gly Lys Glu Phe Phe Pro Met Glu Ala Gln Leu Ser Arg Leu
                325                 330                 335
Val Gly Gln Pro Leu Trp Asp Val Ser Arg Ser Ser Thr Gly Asn Leu
            340                 345                 350
Val Glu Trp Phe Leu Leu Arg Lys Ala Tyr Glu Arg Asn Glu Val Ala
        355                 360                 365
Pro Asn Lys Pro Ser Glu Glu Glu Tyr Glu Arg Arg Leu Arg Glu Ser
        370                 375                 380
Tyr Ala Gly Gly Phe Val Lys Glu Pro Glu Lys Gly Leu Trp Glu Asn
385                 390                 395                 400
Leu Val Tyr Leu Asp Phe Arg Ser Leu Tyr Pro Ser Ile Ile Ile Thr
                405                 410                 415
His Asn Val Ser Pro Asp Thr Leu Asn Arg Glu Gly Cys Arg Glu Tyr
            420                 425                 430
Asp Val Ala Pro Glu Val Gly His Lys Phe Cys Lys Asp Phe Pro Gly
        435                 440                 445
Phe Ile Pro Ser Leu Leu Lys Arg Leu Leu Glu Glu Arg Gln Glu Ile
        450                 455                 460
Lys Thr Lys Met Lys Ala Ser Gln Asp Pro Ile Glu Lys Ile Met Leu
465                 470                 475                 480
Asp Tyr Arg Gln Arg Ala Ile Lys Ile Leu Ala Asn Ser Tyr Tyr Gly
                485                 490                 495
Tyr Tyr Gly Tyr Ala Lys Ala Arg Trp Tyr Cys Lys Glu Cys Ala Glu
            500                 505                 510
Ser Val Thr Ala Trp Gly Arg Glu Tyr Ile Glu Leu Val Arg Lys Glu
        515                 520                 525
Leu Glu Glu Lys Phe Gly Phe Lys Val Leu Tyr Ile Asp Thr Asp Gly
    530                 535                 540
Leu Tyr Ala Thr Ile Pro Gly Gly Glu Pro Glu Glu Ile Lys Lys Lys
545                 550                 555                 560
Ala Leu Glu Phe Val Lys Tyr Ile Asn Ser Lys Leu Pro Gly Leu Leu
                565                 570                 575
Glu Leu Glu Tyr Glu Gly Phe Tyr Val Arg Gly Phe Phe Val Thr Lys
            580                 585                 590
```

```
Lys Arg Tyr Ala Val Ile Asp Glu Glu Gly Lys Ile Ile Thr Arg Gly
            595                 600                 605

Leu Glu Ile Val Arg Arg Asp Trp Ser Glu Ile Ala Lys Glu Thr Gln
        610                 615                 620

Ala Arg Val Leu Glu Ala Ile Leu Lys His Gly Asn Val Glu Glu Ala
625                 630                 635                 640

Val Lys Ile Val Lys Glu Val Thr Gln Lys Leu Ala Lys Tyr Glu Ile
                645                 650                 655

Pro Pro Glu Lys Leu Ala Ile Tyr Glu Gln Ile Thr Arg Pro Leu His
            660                 665                 670

Glu Tyr Lys Ala Ile Gly Pro His Val Ala Val Ala Lys Arg Leu Ala
        675                 680                 685

Ala Arg Gly Val Lys Val Arg Pro Gly Met Val Ile Gly Tyr Ile Val
690                 695                 700

Leu Arg Gly Asp Gly Pro Ile Ser Asn Arg Ala Ile Leu Ala Glu Glu
705                 710                 715                 720

Tyr Asp Leu Lys Lys His Lys Tyr Asp Ala Glu Tyr Tyr Ile Glu Asn
                725                 730                 735

Gln Val Leu Pro Ala Val Leu Arg Ile Leu Glu Ala Phe Gly Tyr Arg
            740                 745                 750

Lys Glu Asp Leu Arg
        755

<210> SEQ ID NO 3
<211> LENGTH: 2535
<212> TYPE: DNA
<213> ORGANISM: Artificial Sequence
<220> FEATURE:
<223> OTHER INFORMATION: Description of Artificial Sequence:hybrid
      enzyme F11 mutant error-correcting polymerase lacking polymerase
      activity retaining 3' to 5' exonuclease activity (pol- exo+)
<220> FEATURE:
<221> NAME/KEY: CDS
<222> LOCATION: (1)..(2535)
<223> OTHER INFORMATION: hybrid enzyme F11

<400> SEQUENCE: 3
atgatcctgg atgctgacta catcactgaa gacggcaaac cgattatccg tctgttcaaa      60
aaagagaacg gcgaatttaa ggttgagtat gatcgcaact ttcgtccata catttacgct     120
ctgctgagag atgattctca gattgatgaa gttaaaaaaa tcactgctga gcgccatggc     180
aagattgttc gtatcattga tgcggaaaag gtagaaaaga aatttctggg cagaccaatc     240
accgtgtgga gactgtattt cgaacatcca caagatgttc cggctattcg cgataaagtt     300
cgcgaacatc ctgcagttgt tgacatcttc gaatacgata ttccatttgc aaagcgttac     360
ctcatcgaca aaggcctgat accaatggag ggcgaggaag aactcaagct cctggcgttc     420
gatatagaaa ccctctatca cgaaggcgaa gagtttggta aggcccaat  tataatgatc     480 agctatgcag atgaaaacga agcaaggtg attacttgga aaaaaataga tctcccatac     540
gttgaggttg tatcttccga cgcgagatg attaagcgct ttctcaaaat tatccgcgag     600
aaggatccgg acgttatcgt tacttataac ggcgactctt ttgacttccc atatctggtg     660
aaacgcgcag aaaaactcgg tattaaactg actatcggcc gtgatggttc cgagccgaag     720
atgcagcgtc tcggcgatat gaccgctgta gaaattaagg tcgtatcca tttcgacctg     780 tatcatgtaa ttcgtcgtac tattaacctc ccgacttaca ctctcgaggc tgtatatgaa     840 gcaattttg gtaagccgaa ggagaaggta tacgccgatg agattgcaga ggcgtgggaa     900
```

-continued

| | |
|---|---|
| tccggtgagg gcctcgagcg tgttgcaaaa tactccatgg aagatgcaaa ggtgacttat | 960 |
| gaactcggca agaattcct cccaatggaa atccagctct ctcgcctggt tggccaacca | 1020 |
| ctgtgggatt ttctcgttc ttccaccggt aacctcgtag agtggtttct cctgcgcaaa | 1080 |
| gcgtacgaac gcaacgaagt ggctccgaac aagccatctg aagaagagta tgaacgccgt | 1140 |
| ctccgcgagt cttacgctgg tggctatgtt aaagagccag aaaagggcct ctgggaaaac | 1200 |
| ctcgtgtacc tcgattttcg ctctctggat ccggacatta tcattaccca caacgtgtct | 1260 |
| ccggatactc tcaaccgcga gggctgcaga gagtatgatg ttgctccgga gtaggccac | 1320 |
| aagttctgca aggacttccc gggctttatt ccgtctctcc tgaaacgtct gctcgaggaa | 1380 |
| cgccaagaga ttaagactaa aatgaaggcg tcccaggatc cgattgaaaa aataatgctc | 1440 |
| gactatcgcc aaagagcgat taaaatcctc gcaaactctt attacggcta ttatggctat | 1500 |
| gcaaaagcac gctggtactg taaggagtgt gctgagtccg ttactgcttg gggtcgcgaa | 1560 |
| tacatcgagc tcgtgcggaa ggagctcgaa gaaaagtttg gctttaaagt tctctacatt | 1620 |
| gacactgatg gtctctatgc gactattccg ggtggtgagc tgaggaaat taagaaaaag | 1680 |
| gctctagaat ttgtgaaata cattaactcg aagctcccgg gtctcctgga gctcgaatat | 1740 |
| gaaggctttt atgttcgcgg cttcttcgtt accaagaaga gatatgcgct gattgatgaa | 1800 |
| gaaggcaaaa ttattactcg tggtctcgag attgtgcgcc gtgattggag cgaaattgcg | 1860 |
| aaagaaactc aagctagagt tctcgagact attctcaaac acggcaacgt tgaagaagct | 1920 |
| gtgagaattg taaagaagt aaccaaaag ctctctaact atgaaattcc gccagagaag | 1980 |
| ctcgcgattt atgagcagat tactcgcccg ctgcatgagt ataaggcgat tggtccgcac | 2040 |
| gtggctgttg caaagagact ggctgctaaa ggcgtgaaaa ttagaccggg tatggtaatt | 2100 |
| ggctacattg tactccgcgg cgatggtccg attagcaacc gtgcaattct agctgaggaa | 2160 |
| tacgatccga aaaagcacaa gtatgacgca gaatattaca ttgagaacca ggtgctcccg | 2220 |
| gcggtactcc gtattctgga ggcttttggc taccgtaagg aagacctccg ctgccaaaag | 2280 |
| actaaacaga ctggcctcac tgcttggctc aacattaaaa aatccggtac cggcggtggc | 2340 |
| ggtgcaaccg taaagttcaa gtacaaaggc aagaaaaag aggtagacat ctccaagatc | 2400 |
| aagaaagtat ggcgtgtggg caagatgatc tccttcacct cgacgagggg cggtggcaag | 2460 |
| accggccgtg gtgcggtaag cgaaaaggac gcgccgaagg agctgctgca gatgctggag | 2520 |
| aagcagaaaa agtga | 2535 |

<210> SEQ ID NO 4
<211> LENGTH: 844
<212> TYPE: PRT
<213> ORGANISM: Artificial Sequence
<220> FEATURE:
<223> OTHER INFORMATION: Description of Artificial Sequence:hybrid
enzyme F11 mutant error-correcting polymerase lacking polymerase
activity retaining 3' to 5' exonuclease activity (pol- exo+)

<400> SEQUENCE: 4

Met Ile Leu Asp Ala Asp Tyr Ile Thr Glu Asp Gly Lys Pro Ile Ile
 1               5                  10                  15

Arg Leu Phe Lys Lys Glu Asn Gly Glu Phe Lys Val Glu Tyr Asp Arg
            20                  25                  30

Asn Phe Arg Pro Tyr Ile Tyr Ala Leu Leu Arg Asp Asp Ser Gln Ile
        35                  40                  45

Asp Glu Val Lys Lys Ile Thr Ala Glu Arg His Gly Lys Ile Val Arg

-continued

```
            50                  55                  60
Ile Ile Asp Ala Glu Lys Val Glu Lys Phe Leu Gly Arg Pro Ile
65                  70                  75                  80

Thr Val Trp Arg Leu Tyr Phe Glu His Pro Gln Asp Val Pro Ala Ile
                85                  90                  95

Arg Asp Lys Val Arg Glu His Pro Ala Val Val Asp Ile Phe Glu Tyr
            100                 105                 110

Asp Ile Pro Phe Ala Lys Arg Tyr Leu Ile Asp Lys Gly Leu Ile Pro
            115                 120                 125

Met Glu Gly Glu Glu Leu Lys Leu Leu Ala Phe Asp Ile Glu Thr
130                 135                 140

Leu Tyr His Glu Gly Glu Glu Phe Gly Lys Gly Pro Ile Ile Met Ile
145                 150                 155                 160

Ser Tyr Ala Asp Glu Asn Glu Ala Lys Val Ile Thr Trp Lys Lys Ile
                165                 170                 175

Asp Leu Pro Tyr Val Glu Val Val Ser Ser Glu Arg Glu Met Ile Lys
            180                 185                 190

Arg Phe Leu Lys Ile Ile Arg Glu Lys Asp Pro Asp Val Ile Val Thr
        195                 200                 205

Tyr Asn Gly Asp Ser Phe Asp Phe Pro Tyr Leu Val Lys Arg Ala Glu
        210                 215                 220

Lys Leu Gly Ile Lys Leu Thr Ile Gly Arg Asp Gly Ser Glu Pro Lys
225                 230                 235                 240

Met Gln Arg Leu Gly Asp Met Thr Ala Val Glu Ile Lys Gly Arg Ile
                245                 250                 255

His Phe Asp Leu Tyr His Val Ile Arg Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala Asp Glu Ile Ala Glu Ala Trp Glu Ser Gly Glu Gly
        290                 295                 300

Leu Glu Arg Val Ala Lys Tyr Ser Met Glu Asp Ala Lys Val Thr Tyr
305                 310                 315                 320

Glu Leu Gly Lys Glu Phe Leu Pro Met Glu Ile Gln Leu Ser Arg Leu
                325                 330                 335

Val Gly Gln Pro Leu Trp Asp Val Ser Arg Ser Ser Thr Gly Asn Leu
            340                 345                 350

Val Glu Trp Phe Leu Leu Arg Lys Ala Tyr Glu Arg Asn Glu Val Ala
        355                 360                 365

Pro Asn Lys Pro Ser Glu Glu Glu Tyr Glu Arg Arg Leu Arg Glu Ser
        370                 375                 380

Tyr Ala Gly Gly Tyr Val Lys Glu Pro Glu Lys Gly Leu Trp Glu Asn
385                 390                 395                 400

Leu Val Tyr Leu Asp Phe Arg Ser Leu Asp Pro Ile Ile Ile Thr
                405                 410                 415

His Asn Val Ser Pro Asp Thr Leu Asn Arg Glu Gly Cys Arg Glu Tyr
            420                 425                 430

Asp Val Ala Pro Glu Val Gly His Lys Phe Cys Lys Asp Phe Pro Gly
        435                 440                 445

Phe Ile Pro Ser Leu Leu Lys Arg Leu Leu Glu Glu Arg Gln Glu Ile
        450                 455                 460

Lys Thr Lys Met Lys Ala Ser Gln Asp Pro Ile Glu Lys Ile Met Leu
465                 470                 475                 480
```

Asp Tyr Arg Gln Arg Ala Ile Lys Ile Leu Ala Asn Ser Tyr Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Glu Tyr Ile Glu Leu Val Arg Lys Glu
            515                 520                 525

Leu Glu Glu Lys Phe Gly Phe Lys Val Leu Tyr Ile Asp Thr Asp Gly
        530                 535                 540

Leu Tyr Ala Thr Ile Pro Gly Gly Glu Pro Glu Glu Ile Lys Lys Lys
545                 550                 555                 560

Ala Leu Glu Phe Val Lys Tyr Ile Asn Ser Lys Leu Pro Gly Leu Leu
            565                 570                 575

Glu Leu Glu Tyr Glu Gly Phe Tyr Val Arg Gly Phe Phe Val Thr Lys
            580                 585                 590

Lys Arg Tyr Ala Leu Ile Asp Glu Gly Lys Ile Ile Thr Arg Gly
        595                 600                 605

Leu Glu Ile Val Arg Arg Asp Trp Ser Glu Ile Ala Lys Glu Thr Gln
610                 615                 620

Ala Arg Val Leu Glu Thr Ile Leu Lys His Gly Asn Val Glu Glu Ala
625                 630                 635                 640

Val Arg Ile Val Lys Glu Val Thr Lys Lys Leu Ser Asn Tyr Glu Ile
            645                 650                 655

Pro Pro Glu Lys Leu Ala Ile Tyr Glu Gln Ile Thr Arg Pro Leu His
            660                 665                 670

Glu Tyr Lys Ala Ile Gly Pro His Val Ala Val Ala Lys Arg Leu Ala
        675                 680                 685

Ala Lys Gly Val Lys Ile Arg Pro Gly Met Val Ile Gly Tyr Ile Val
        690                 695                 700

Leu Arg Gly Asp Gly Pro Ile Ser Asn Arg Ala Ile Leu Ala Glu Glu
705                 710                 715                 720

Tyr Asp Pro Lys Lys His Lys Tyr Asp Ala Glu Tyr Tyr Ile Glu Asn
                725                 730                 735

Gln Val Leu Pro Ala Val Leu Arg Ile Leu Glu Ala Phe Gly Tyr Arg
            740                 745                 750

Lys Glu Asp Leu Arg Cys Gln Lys Thr Lys Gln Thr Gly Leu Thr Ala
            755                 760                 765

Trp Leu Asn Ile Lys Lys Ser Gly Thr Gly Gly Gly Ala Thr Val
770                 775                 780

Lys Phe Lys Tyr Lys Gly Glu Glu Lys Glu Val Asp Ile Ser Lys Ile
785                 790                 795                 800

Lys Lys Val Trp Arg Val Gly Lys Met Ile Ser Phe Thr Tyr Asp Glu
            805                 810                 815

Gly Gly Gly Lys Thr Gly Arg Gly Ala Val Ser Glu Lys Asp Ala Pro
            820                 825                 830

Lys Glu Leu Leu Gln Met Leu Glu Lys Gln Lys Lys
        835                 840

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence:beta
      glucuronidase (GUSB101) exemplary probe to target with TCAGC
      preferred bases hybridizing to target included at 3' end adjacent -continued

```
      to 3' nucleotide mismatched to template
<220> FEATURE:
<221> NAME/KEY: modified_base
<222> LOCATION: (1)
<223> OTHER INFORMATION: n = t modified by FAM
<220> FEATURE:
<221> NAME/KEY: modified_base
<222> LOCATION: (22)
<223> OTHER INFORMATION: n = t modified by "Black hole quencher" BHQ-1

<400> SEQUENCE: 5
ngggcactgc caatcctcag cn                                                    22

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence:
      phosphoglycerate kinase I (PGK101) exemplary probe to target with
      TCAGC preferred bases hybridizing to target included at 3' end
      adjacent to 3' nucleotide mismatched to template
<220> FEATURE:
<221> NAME/KEY: modified_base
<222> LOCATION: (1)
<223> OTHER INFORMATION: n = a modified by FAM
<220> FEATURE:
<221> NAME/KEY: modified_base
<222> LOCATION: (25)
<223> OTHER INFORMATION: n = a modified by "Black hole quencher" BHQ-1

<400> SEQUENCE: 6
natcttcaca ccattcttct cagcn                                                 25

<210> SEQ ID NO 7
<211> LENGTH: 26
<212> TYPE: DNA
<213> ORGANISM: Artificial Sequence
<220> FEATURE:
<223> OTHER INFORMATION: Description of Artificial Sequence:transferrin
      receptor (TFRC101) exemplary probe to target with TCAGC preferred
      bases hybridizing to target included at 3' end adjacent to
      3' nucleotide mismatched to template
<220> FEATURE:
<221> NAME/KEY: modified_base
<222> LOCATION: (1)
<223> OTHER INFORMATION: n = t modified by FAM
<220> FEATURE:
<221> NAME/KEY: modified_base
<222> LOCATION: (26)
<223> OTHER INFORMATION: n = t modified by "Black hole quencher" BHQ-1

<400> SEQUENCE: 7
ngacaaatct gtctgttttc tcagcn                                                26

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence:large
      ribosomal protein (RPLP107) exemplary probe to target with TCAGC
      preferred bases hybridizing to target included at 3' end adjacent
      to 3' nucleotide mismatched to template
<220> FEATURE:
<221> NAME/KEY: modified_base
<222> LOCATION: (1)
<223> OTHER INFORMATION: n = a modified by FAM
<220> FEATURE:
<221> NAME/KEY: modified_base
<222> LOCATION: (23)
<223> OTHER INFORMATION: n = t modified by "Black hole quencher" BHQ-1
```

<400> SEQUENCE: 8
ngaaggcctt gacctttca gcn                                              23

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence:
      glyceraldehyde 3-phosphate dehydrogenase (GAPD) exemplary probe to
      target with TCAGC preferred bases hybridizing to target included
      at 3' end adjacent to 3' nucleotide mismatched to template
<220> FEATURE:
<221> NAME/KEY: modified_base
<222> LOCATION: (1)
<223> OTHER INFORMATION: n = c modified by cyanine dye Cy5
<220> FEATURE:
<221> NAME/KEY: modified_base
<222> LOCATION: (20)
<223> OTHER INFORMATION: n = t modified by "Black hole quencher" BHQ-2

<400> SEQUENCE: 9
naagcttccc gttctcagcn                                                 20

<210> SEQ ID NO 10
<211> LENGTH: 15
<212> TYPE: DNA
<213> ORGANISM: Artificial Sequence
<220> FEATURE:
<223> OTHER INFORMATION: Description of Artificial Sequence:5' portion
      of succinate dehydrogenase subunit A (SDHA) exemplary probe to
      target with multiple mismatches at 3' end, abasic site and
      internal label
<220> FEATURE:
<221> NAME/KEY: modified_base
<222> LOCATION: (1)
<223> OTHER INFORMATION: n = g modified by quencher (Q)
<220> FEATURE:
<221> NAME/KEY: modified_base
<222> LOCATION: (15)
<223> OTHER INFORMATION: n = g 3' modified by SEQ ID NO:11 via
      phosphodiester bond to deoxyribose abasic site ("0")

<400> SEQUENCE: 10
ntcatgcagg cctgn                                                      15

<210> SEQ ID NO 11
<211> LENGTH: 18
<212> TYPE: DNA
<213> ORGANISM: Artificial Sequence
<220> FEATURE:
<223> OTHER INFORMATION: Description of Artificial Sequence:3' portion
      of succinate dehydrogenase subunit A (SDHA) exemplary probe to
      target with multiple mismatches at 3' end, abasic site and
      internal label
<220> FEATURE:
<221> NAME/KEY: modified_base
<222> LOCATION: (1)
<223> OTHER INFORMATION: n = g 5' modified by SEQ ID NO:10 via
      phosphodiester bond to deoxyribose abasic site ("0")
<220> FEATURE:
<221> NAME/KEY: modified_base
<222> LOCATION: (14)
<223> OTHER INFORMATION: n = t modified by a label (internal label)

<400> SEQUENCE: 11
nataaagtcc ctcngcat                                                   18

<210> SEQ ID NO 12
<211> LENGTH: 17
<212> TYPE: DNA

```
<213> ORGANISM: Artificial Sequence
<220> FEATURE:
<223> OTHER INFORMATION: Description of Artificial Sequence:5' portion
      of hydroxymethyl-bilane synthase (HMBS) exemplary probe to target
      with multiple mismatches at  3' end, abasic site and internal
      label
<220> FEATURE:
<221> NAME/KEY: modified_base
<222> LOCATION: (1)
<223> OTHER INFORMATION: n = a modified by quencher (Q)
<220> FEATURE:
<221> NAME/KEY: modified_base
<222> LOCATION: (17)
<223> OTHER INFORMATION: n = c 3' modified by SEQ ID NO:13 via
      phosphodiester bond to deoxyribose abasic site ("0")

<400> SEQUENCE: 12
ngcctcgtac cctggcn                                                   17

<210> SEQ ID NO 13
<211> LENGTH: 15
<212> TYPE: DNA
<213> ORGANISM: Artificial Sequence
<220> FEATURE:
<223> OTHER INFORMATION: Description of Artificial Sequence:3' portion
      of hydroxymethyl-bilane synthase (HMBS) exemplary probe to target
      with multiple mismatches at  3' end, abasic site and internal
      label
<220> FEATURE:
<221> NAME/KEY: modified_base
<222> LOCATION: (1)
<223> OTHER INFORMATION: n = g 5' modified by SEQ ID NO:12 via
      phosphodiester bond to deoxyribose abasic site ("0")
<220> FEATURE:
<221> NAME/KEY: modified_base
<222> LOCATION: (11)
<223> OTHER INFORMATION: n = t modified by label (internal label)

<400> SEQUENCE: 13
ncagtttgaa ntttt                                                     15

<210> SEQ ID NO 14
<211> LENGTH: 11
<212> TYPE: DNA
<213> ORGANISM: Artificial Sequence
<220> FEATURE:
223> OTHER INFORMATION: Description of Artificial Sequence:5' portion of
      TATA box-binding protein (TBP) exemplary probe to target with
      multiple mismatches at  3' end, abasic site and internal label
<220> FEATURE:
<221> NAME/KEY: modified_base
<222> LOCATION: (1)
<223> OTHER INFORMATION: n = c modified by quencher (Q)
<220> FEATURE:
<221> NAME/KEY: modified_base
<222> LOCATION: (11)
<223> OTHER INFORMATION: n = c 3' modified by SEQ ID NO:15 via
      phosphodiester bond to deoxyribose abasic site ("0")

<400> SEQUENCE: 14
nctggtgcca n                                                         11

<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence:3' portion
      of TATA box-binding protein (TBP) exemplary probe to target with
      multiple mismatches at  3' end, abasic site and internal label
<220> FEATURE:
<221> NAME/KEY: modified_base
<222> LOCATION: (1)
```

-continued

```
<223> OTHER INFORMATION: n = c 5' modified by SEQ ID NO:14 via
      phosphodiester bond to deoxyribose abasic site ("0")
<220> FEATURE:
<221> NAME/KEY: modified_base
<222> LOCATION: (12)
<223> OTHER INFORMATION: n = t modified by label (internal label)

<400> SEQUENCE: 15
ncctgcaact cntccagga                                                  19

<210> SEQ ID NO 16
<211> LENGTH: 13
<212> TYPE: DNA
<213> ORGANISM: Artificial Sequence
<220> FEATURE:
<223> OTHER INFORMATION: Description of Artificial Sequence:5' portion
      of ubiquitin C (UBC) exemplary probe to target with multiple
      mismatches at 3' end, abasic site and internal label
<220> FEATURE:
<221> NAME/KEY: modified_base
<222> LOCATION: (1)
<223> OTHER INFORMATION: n = g modified by quencher (Q)
<220> FEATURE:
<221> NAME/KEY: modified_base
<222> LOCATION: (13)
<223> OTHER INFORMATION: n = c 3' modified by SEQ ID NO:17 via
      phosphodiester bond to deoxyribose abasic site ("0")

<400> SEQUENCE: 16
natctgcatt gtn                                                        13

<210> SEQ ID NO 17
<211> LENGTH: 18
<212> TYPE: DNA
<213> ORGANISM: Artificial Sequence
<220> FEATURE:
<223> OTHER INFORMATION: Description of Artificial Sequence:3' portion
      of ubiquitin C (UBC) exemplary probe to target with multiple
      mismatches at 3' end, abasic site and internal label
<220> FEATURE:
<221> NAME/KEY: modified_base
<222> LOCATION: (1)
<223> OTHER INFORMATION: n = a 5' modified by SEQ ID NO:16 via
      phosphodiester bond to deoxyribose abasic site ("0")
<220> FEATURE:
<221> NAME/KEY: modified_base
<222> LOCATION: (16)
<223> OTHER INFORMATION: n = t modified by label (internal label)

<400> SEQUENCE: 17
ngtgacgatc acagancc                                                   18

<210> SEQ ID NO 18
<211> LENGTH: 12
<212> TYPE: DNA
<213> ORGANISM: Artificial Sequence
<220> FEATURE:
<223> OTHER INFORMATION: Description of Artificial Sequence:5' portion
      of ribonucleotide reductase M1 polypeptide (RRM) exemplary probe
      to target with multiple mismatches at 3' end, abasic site and
      internal label
<220> FEATURE:
<221> NAME/KEY: modified_base
<222> LOCATION: (1)
<223> OTHER INFORMATION: n = c modified by quencher (Q)
<220> FEATURE:
<221> NAME/KEY: modified_base
<222> LOCATION: (12)
<223> OTHER INFORMATION: n = c 3' modified by SEQ ID NO:19 via
      phosphodiester bond to deoxyribose abasic site ("0")

<400> SEQUENCE: 18
```
ncaccttgat cn                                                              12

<210> SEQ ID NO 19
<211> LENGTH: 19
<212> TYPE: DNA
<213> ORGANISM: Artificial Sequence
<220> FEATURE:
<223> OTHER INFORMATION: Description of Artificial Sequence:3' portion
      of ribonucleotide reductase M1 polypeptide (RRM) exemplary probe
      to target with multiple mismatches at 3' end, abasic site and
      internal label
<220> FEATURE:
<221> NAME/KEY: modified_base
<222> LOCATION: (1)
<223> OTHER INFORMATION: n = c 5' modified by SEQ ID NO:18 via
      phosphodiester bond to deoxyribose abasic site ("0")

<400> SEQUENCE: 19
natatctagc tgtnggtgg                                                       19

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence:TaqMan Probe
<220> FEATURE:
<221> NAME/KEY: modified_base
<222> LOCATION: (1)
<223> OTHER INFORMATION: n = c modified by cyanine dye Cy5
<220> FEATURE:
<221> NAME/KEY: modified_base
<222> LOCATION: (20)
<223> OTHER INFORMATION: n = c modified by "Black hole quencher" BHQ-2

<400> SEQUENCE: 20
naagcttccc gttctcagcn                                                      20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence:Proofreading
      assay Probe
<220> FEATURE:
<221> NAME/KEY: modified_base
<222> LOCATION: (1)
<223> OTHER INFORMATION: n = c modified by cyanine dye Cy5
<220> FEATURE:
<221> NAME/KEY: modified_base
<222> LOCATION: (19)..(20)
<223> OTHER INFORMATION: c at position 19 linked to g at position 20 via
      phosphorthioate linkage
<220> FEATURE:
<221> NAME/KEY: modified_base
<222> LOCATION: (20)
<223> OTHER INFORMATION: n = g modified by "Black hole quencher" BHQ-2

<400> SEQUENCE: 21
naagcttccc gttctcagcn                                                      20

<210> SEQ ID NO 22
<211> LENGTH: 23
<212> TYPE: DNA
<213> ORGANISM: Artificial Sequence
<220> FEATURE:
<223> OTHER INFORMATION: Description of Artificial Sequence:
      beta2-microglobulin (B2M) probe
<220> FEATURE:
<221> NAME/KEY: modified_base
<222> LOCATION: (1)

<223> OTHER INFORMATION: n = c modified by FAM
<220> FEATURE:
<221> NAME/KEY: modified_base
<222> LOCATION: (23)
<223> OTHER INFORMATION: n = a modified by "black hole quencher" BHQ-1

<400> SEQUENCE: 22
ntttggagta cgctggatag ccn                                              23

<210> SEQ ID NO 23
<211> LENGTH: 19
<212> TYPE: DNA
<213> ORGANISM: Artificial Sequence
<220> FEATURE:
<223> OTHER INFORMATION: Description of Artificial Sequence:
      amplification primer UBCFS
<220> FEATURE:
<221> NAME/KEY: modified_base
<222> LOCATION: (18)..(19)
<223> OTHER INFORMATION: t at position 18 linked to g at position 19 via
      phosphorthioate linkage

<400> SEQUENCE: 23
atttgggtcg cggttcttg                                                   19

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence:
      amplification primer UBCRS
<220> FEATURE:
<221> NAME/KEY: modified_base
<222> LOCATION: (20)..(21)
<223> OTHER INFORMATION: g at position 20 linked to t at position 21 via
      phosphorthioate linkage

<400> SEQUENCE: 24
tgccttgaca ttctcgatgg t                                                21

<210> SEQ ID NO 25
<211> LENGTH: 13
<212> TYPE: DNA
<213> ORGANISM: Artificial Sequence
<220> FEATURE:
<223> OTHER INFORMATION: Description of Artificial Sequence:5' portion
      of UBCiFlp4 probe
<220> FEATURE:
<221> NAME/KEY: modified_base
<222> LOCATION: (1)
<223> OTHER INFORMATION: n = g modified by Iowa Black Quencher (5IabFQ)
<220> FEATURE:
<221> NAME/KEY: modified_base
<222> LOCATION: (13)
<223> OTHER INFORMATION: n = c 3' modified by SEQ ID NO:26 via
      phosphodiester bond to deoxyribose internal abasic site ("idSp")

<400> SEQUENCE: 25
natctgcatt gtn                                                         13

<210> SEQ ID NO 26
<211> LENGTH: 18
<212> TYPE: DNA
<213> ORGANISM: Artificial Sequence
<220> FEATURE:
<223> OTHER INFORMATION: Description of Artificial Sequence:3' portion
      of UBCiFlp4 probe
<220> FEATURE:
<221> NAME/KEY: modified_base
<222> LOCATION: (1)

```
<223> OTHER INFORMATION: n = a 5' modified by SEQ ID NO:25 via
      phosphodiester bond to deoxyribose abasic site ("idSp")
<220> FEATURE:
<221> NAME/KEY: modified_base
<222> LOCATION: (16)
<223> OTHER INFORMATION: n = t modified by fluorescein (iFluorT)
      internal label

<400> SEQUENCE: 26
ngtgacgatc acagancc                                                         18

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence:dual
      lableled GAPD-G) probe for double-stranded substrate activity
      (DS-Exo assay) and single-stranded substrate (SS-Exo assay)
<220> FEATURE:
<221> NAME/KEY: modified_base
<222> LOCATION: (1)
<223> OTHER INFORMATION: n = c modified by cyanine dye Cy5
<220> FEATURE:
<221> NAME/KEY: modified_base
<222> LOCATION: (20)
<223> OTHER INFORMATION: n = g modified by "Black hole quencher" BHQ-2

<400> SEQUENCE: 27
naagcttccc gttctcagcn                                                       20

<210> SEQ ID NO 28
<211> LENGTH: 29
<212> TYPE: DNA
<213> ORGANISM: Artificial Sequence
<220> FEATURE:
<223> OTHER INFORMATION: Description of Artificial Sequence:
      complementary oligo for double-stranded substrate activity
      (DS-Exo assay)

<400> SEQUENCE: 28
gcaccgtcaa gctgagaacg ggaagcttg                                             29

<210> SEQ ID NO 29
<211> LENGTH: 4
<212> TYPE: PRT
<213> ORGANISM: Artificial Sequence
<220> FEATURE:
<223> OTHER INFORMATION: Description of Artificial Sequence:mutant YxGG
      motif sequence from A6YX1

<400> SEQUENCE: 29

Thr Thr Gly Gly
  1

<210> SEQ ID NO 30
<211> LENGTH: 4
<212> TYPE: PRT
<213> ORGANISM: Artificial Sequence
<220> FEATURE:
<223> OTHER INFORMATION: Description of Artificial Sequence:mutant YxGG
      motif sequence from A6YX2, F11deltaYX2KNY and
      F11deltaXY2Y

<400> SEQUENCE: 30

Asp Thr Gly Gly
  1

<210> SEQ ID NO 31
```

```
<211> LENGTH: 4
<212> TYPE: PRT
<213> ORGANISM: Artificial Sequence
<220> FEATURE:
<223> OTHER INFORMATION: Description of Artificial Sequence:mutant YxGG
      motif sequence from A6YX3

<400> SEQUENCE: 31

Asn Thr Gly Gly
 1

<210> SEQ ID NO 32
<211> LENGTH: 4
<212> TYPE: PRT
<213> ORGANISM: Artificial Sequence
<220> FEATURE:
<223> OTHER INFORMATION: Description of Artificial Sequence:mutant YxGG
      motif sequence from F11deltaSNL1

<400> SEQUENCE: 32

Asn Leu Gly Gly
 1

<210> SEQ ID NO 33
<211> LENGTH: 4
<212> TYPE: PRT
<213> ORGANISM: Artificial Sequence
<220> FEATURE:
<223> OTHER INFORMATION: Description of Artificial Sequence:mutant YxGG
      motif sequence from F11deltaYX2

<400> SEQUENCE: 33

Ser Thr Gly Gly
 1

<210> SEQ ID NO 34
<211> LENGTH: 4
<212> TYPE: PRT
<213> ORGANISM: Artificial Sequence
<220> FEATURE:
<223> OTHER INFORMATION: Description of Artificial Sequence:mutant YxGG
      motif sequence from F11deltaYX3

<400> SEQUENCE: 34

Thr Ala Gly Gly
 1

<210> SEQ ID NO 35
<211> LENGTH: 4
<212> TYPE: PRT
<213> ORGANISM: Artificial Sequence
<220> FEATURE:
<223> OTHER INFORMATION: Description of Artificial Sequence:wild-type
      YxGG motif sequence from A6, F11delta, F11deltaK or F11deltaY

<400> SEQUENCE: 35

Tyr Ala Gly Gly
 1
```

QUANTITATIVE AMPLIFICATION WITH A LABELED PROBE AND 3' TO 5' EXONUCLEASE ACTIVITY

CROSS-REERENCE TO RELATED APPLICATIONS

This application claims the benefit of U.S. Provisional Application No. 60/559,137, filed Apr. 1, 2004, which is herein incorporated by referenced.

BACKGROUND OF THE INVENTION

Various techniques for performing quantitative amplification of a nucleic acid are known. These techniques include use of 5' to 3' exonuclease assays, e.g., Taqman™ probes (see, e.g., U.S. Pat. Nos. 5,210,015 and 5,487,972, Heid et al., *Genome Res.* 6:986-994, 1996; Holland et al., *Proc. Nat'l Acad. Sci. USA* 88:7276-7280, 1991; and Lee et al., *Nuc. Acids Res.* 21:3761-3766, 1993). Other methodologies employ one or more probe oligonucleotides that are structured such that a change in fluorescence is generated when the oligonucleotide(s) is hybridized to a target nucleic acid. For example, one such method involves a dual fluorophore approach that exploits fluorescence resonance energy transfer (FRET), e.g., LightCycler™ hybridization probes, where two oligo probes anneal to the amplicon (e.g. U.S. Pat. No. 6,174, 670). The oligonucleotides are designed to hybridize in a head-to-tail orientation with the fluorophores separated at a distance that is compatible with efficient energy transfer. Other examples of labeled oligonucleotides that are structured to emit a signal when bound to a nucleic acid or incorporated into an extension product include: Scorpions™ probes (e.g., Whitcombe et al., *Nature Biotechnology* 17:804-807, 1999, and U.S. Pat. No. 6,326,145), Sunrise (or Ampliflour™) primers (e.g., Nazarenko et al., *Nuc. Acids Res.* 25:2516-2521, 1997, and U.S. Pat. No. 6,117,635), LUX™ primers and Molecular Beacons™ probes (e.g., Tyagi et al., *Nature Biotechnology* 14:303-308, 1996 and U.S. Pat. No. 5,989,823).

Real-time PCR methods that are based on the use of hybridization probes have drawbacks, however, when it is desirable to use a proofreading polymerase in the amplification reaction. For example, the presence of a 3' to 5' exonuclease activity can lead to problems due to degradation of the probe.

Nucleic acid detection methods exist that employ error-correcting enzymes. For example, some amplification reactions rely on proofreading activity to detect differences, e.g., polymorphisms or mutations, between nucleic acid sequences (see, e.g., U.S. Pat. No. 5,391,480). In general, such an assay involves labeling the 3' nucleotide in a primer with a fluorescent marker. The labeled oligonucleotide is hybridized to an unknown DNA sample. If the 3' nucleotide (the query position) of the oligonucleotide is complementary to the corresponding nucleotide in the hybridized DNA, it will be insensitive to nuclease; if there is a mismatch it will be sensitive to nuclease and will be cleaved. Clipped-off fluorescent nucleotides are detected, e.g., by a decrease in fluorescence polarization (FP). In these types of assays, at least one of the primers that amplify the target is labeled.

The current invention provides a new method of quantifying an amplification reaction. The method employs a labeled hybridization probe, which is used in an amplification reaction with a polymerase and an enzyme that has 3' to 5' exonuclease activity, e.g., an error-correcting polymerase. The method is distinct from methods employing a 3' to 5' exonuclease activity that are in the prior art. For example, the methods of the present invention employ a labeled hybridization probe and unlabeled amplification primers. Further, the method is generally useful to quantify a PCR reaction, and is not limited to the detection of polymorphisms or mutations.

BRIEF SUMMARY OF THE INVENTION

The invention provides a new method of performing quantitative amplification reactions. The method employs a probe, an enzyme having polymerase activity, and an enzyme having 3' to 5' exonuclease activity. Often, the 3' nucleotide of the probe is a mismatch. The 3' nucleotide is cleaved from the probe during the amplification reaction. The reaction is quantified by detecting the amount of cleavage product that is released during the reaction.

The invention therefore provides a method of quantifying a target nucleic acid in an amplification reaction, the method comprising: incubating a template comprising the target nucleic acid with amplification primers, a probe, a polymerase, and an enzyme having 3' to 5' exonuclease activity under conditions in which the amplification primers and probe specifically hybridize to the target nucleic acid template and the amplification primers are extended by the polymerase to amplify the target nucleic acid, wherein the 3' nucleotide is cleaved from the probe when the probe is specifically hybridized to the target nucleic acid; and detecting the cleavage product, thereby quantifying the target nucleic acid. Typically, the amplification reaction is a polymerase chain reaction. The amplification reaction can also be a multiplex reaction in which multiple targets are identified.

In typical embodiments, the 3' nucleotide is linked to a detection moiety. In other embodiments, a detection moiety is linked to an internal nucleotide. The 3' nucleotide is often a mismatch to the target nucleic acid sequence, e.g., at an invariant (nonpolymorphic) position of the target nucleic acid sequence. In some embodiments, additional 3' nucleotides, e.g., two, three, four, five, six, or seven or more 3' nucleotides, can also be mismatched to the target nucleic acid. In some embodiments, the additional mismatches form a stem-loop structure with upstream probe sequences prior to hybridization with the target nucleic acid sequence.

In some embodiments, the probe comprises a TCAGC at the 3' end adjacent to the 3' mismatched nucleotide. The TCAGC typically matches the target nucleic acid sequence. In other embodiments, the probe comprises an abasic site, e.g., in the middle third of the probe. In other embodiments, the probe comprises an abasic site and an internal nucleotide that is labeled. The probe can also comprise an abasic site, an internal label, and one or more, e.g., two, three, four, five, six, or seven or more, 3' mismatched nucleotides.

The amount of cleaved 3' nucleotide, i.e., cleavage product generated during the reaction, can be detected using a number of assays, particularly those that detect a change in fluorescence when the nucleotide is cleaved, e.g., fluorescence intensity, fluorescence polarization, fluorescence energy transfer, etc.

In some embodiments, the enzyme having 3' to 5' exonuclease activity and the polymerase are the same polypeptide. Often, the enzyme is a proofreading polymerase that supplies both the 3' to 5' exonuclease activity and the polymerase activity. In other embodiments, they are different polypeptides. In an exemplary embodiment, the 3' to 5' exonuclease activity is provided by a mutant error-correcting polymerase that does not have polymerase activity or has significantly reduced polymerase activity compared to a parent polymerase, e.g., a polymerase having a polymerase sequence shown in SEQ ID NO:2 or SEQ ID NO:4. In further embodiments, the mutant error-correcting polymerase (that lacks substantial polymerase activity) may have an increase in the ratio of doubled-stranded exonuclease activity to single-stranded exonuclease activity relative to the parent error-correcting polymerase. In particular embodiments, the mutant error-correcting polymerase has a mutation in the YxGG motif or in the dNTP binding motif that results in an enhanced, relative to the parent protein, ratio of exonuclease activity towards a double-stranded nucleic acid substrate to exonuclease activity towards a single-stranded nucleic acid substrate. Thus, in exemplary embodiments, the mutant error-correcting polymerase has a polymerase sequence as shown in SEQ ID NO:2 or SEQ ID NO:4 where there is a mutation in the YxGG motif or the dNTP binding motif that results in an increase in the ratio of exonuclease activity towards a double-stranded nucleic acid substrate to exonuclease activity towards a single-stranded nucleic acid substrate relative to the polypeptide of SEQ ID NO:2 or SEQ ID NO:4.

Often the enzymes are thermostable. Further, the polymerase and/or enzyme having 3' to 5' exonuclease activity can be a hot-start enzyme.

Exemplary polymerases that can be used in the methods of the invention include a family A polymerase, e.g., in some embodiments, a family A polymerase that is deficient in 5' to 3' exonuclease activity, or that does not have 5' to 3' exonuclease activity; or a family B polymerase, such as *Pyrococcus furiosus* (Pfu); or a hybrid protein, e.g., a polymerase hybrid in which one of the parent polymerases is a family B polymerase such as Pfu poymerase. Additionally, the polymerase can comprise a sequence nonspecific double stranded nucleic acid binding domain, such as an Sso 7 domain, e.g., a Sso7d, Sac7d, or Sac7e domain. In one embodiment, the polymerase is a hybrid polymerase engineered from a Pfu parent polymerase that also comprises an Sso7 domain, e.g., Sso7d, Sac7d, or Sac7e.

The probe can be single-labeled, e.g., with a fluorescent moiety at the 3' end or at an internal residue near the 3' end (such as within 10 nucleotides); but is often double-labeled with two interacting moieties, one of which is often on the 3' end. Examples of double labels that can interact include two fluorescent molecules that interact to change fluorescence, or a fluorescent moiety and quenching moiety. In embodiments that employ a fluorescent label and a quencher, either the label or the quencher can be at the 3' end (or at an internal nucleotide) of the oligonucleotide probe. The second label can be located either internally in the probe or at the 5' end of the probe, accordingly. A label at the end, e.g., the 3' end can be attached to the nucleotide or to the backbone.

In another embodiment, the probe can comprise a minor groove binder (MGB). In an exemplary embodiment, the MGB is on the 5' end of the probe.

Further, the probe can optionally comprise one or more phosphorothioate linkages. For example, the phosphorothioate linkage is often positioned at the 3' end between the last and the second to last nucleotide.

The amount of cleavage product generated during the reaction can be determined by a number of methods, including, but not limited to, fluorescence intensity, fluorescence polarization, and mass spectroscopy. Often, the amount of starting target nucleic acid present in the reaction mixture is quantified by cycle threshold (Ct).

BRIEF DESCRIPTION OF THE DRAWINGS

FIG. 7 shows exemplary probes (SEQ ID NOS:5-9) to target nucleic acids where the probe sequence has a TCAGC (that hybridizes to the target nucleic acid), which is included at the 3' end of the probe adjacent to the mismatched 3' nucleotide.

FIG. 10 provides exemplary probes (SEQ ID NOS:10 and 11, 12 and 13, 14 and 15, 16 and 17, and 18 and 19, respectively) to target sequences where the probes have multiple mismatched nucleotides at the 3' end and include an abasic site. The label is an internal label.

DETAILED DESCRIPTION OF THE INVENTION

Figure 1:
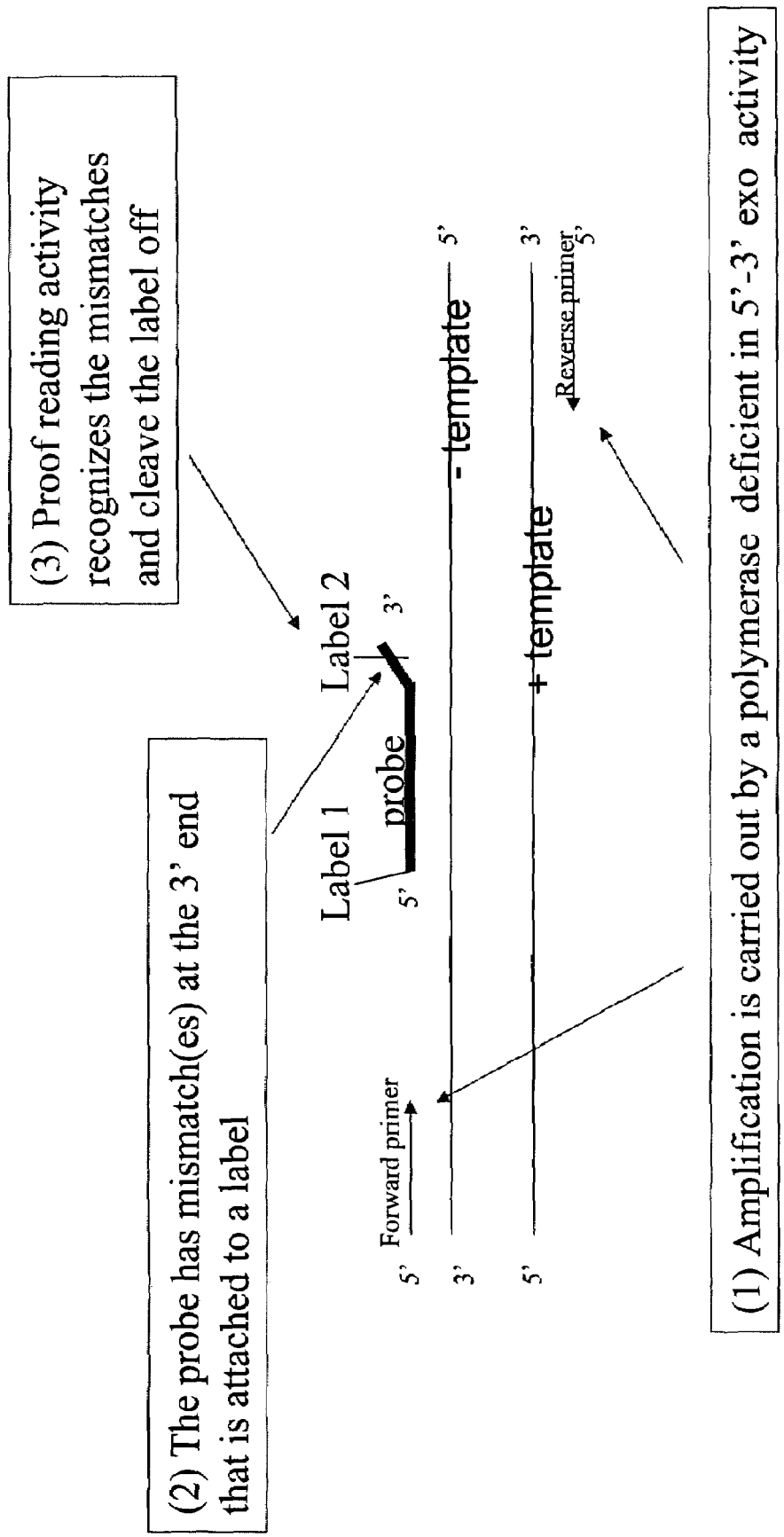
FIG. 1 provides an embodiment of the invention that illustrates the general method.

The invention provides a new method of performing quantitative PCR. The method involves the use of an oligonucleotide probe that is cleaved from the 3' end. The probe is a component of an amplification reaction that employs an enzyme having polymerase activity and an enzyme having 3' to 5' exonuclease activity. Often, a proofreading polymerase can be employed in the reaction, which therefore supplies both the polymerase and 3' to 5' exonuclease activities. The general principle of the invention is illustrated in the embodiment depicted in FIG. 1.

Definitions

A "polymerase" refers to an enzyme that catalyzes polynucleotide synthesis by addition of nucleotide units to a nucleotide chain using DNA or RNA as a template. The term refers to either a complete enzyme or a catalytic domain.

"Domain" refers to a unit of a protein or protein complex, comprising a polypeptide subsequence, a complete polypeptide sequence, or a plurality of polypeptide sequences where that unit has a defined function. The function is understood to be broadly defined and can be ligand binding, catalytic activity or can have a stabilizing effect on the structure of the protein.

The term "3' to 5' exonuclease" or "3' to 5' exonuclease activity" refers to a protein or domain of a protein that catalyzes the stepwise removal of mononucleotides from 3'-termini of DNA molecules.

"Error-correcting activity" refers to a 3' to 5' exonuclease proofreading activity. A proofreading activity preferentially removes a mismatched nucleotide, i.e., the amount of nucleotide that is removed from the 3' end by the proofreading enzyme is greater when the 3' nucleotide is mismatched compared (under the same reaction conditions) to when the 3' nucleotide matches. Typically, the term is used in reference to a template-specific nucleic acid polymerase whereby nucleotides that do not form Watson-Crick base pairs with the template are removed from the 3' end of an oligonucleotide, i.e., a strand being synthesized from a template, in a sequential manner. Examples of polymerases that have error-correcting activity include polymerases from *Pyrococcus furiosus, Thermococcus litoralis*, and *Thermotoga maritima*.

"Sequence-non-specific nucleic-acid-binding domain" refers to a protein domain which binds with significant affinity to a nucleic acid, for which there is no known nucleic acid which binds to the protein domain with more than 100-fold more affinity than another nucleic acid with the same nucleotide composition but a different nucleotide sequence.

"Fused" refers to linkage by covalent bonding.

"Heterologous", when used with reference to portions of a protein, indicates that the protein comprises two or more domains that are not found in the same relationship to each other in nature. Such a protein, e.g., a fusion protein, contains two or more domains from unrelated proteins arranged to make a new functional protein.

"Join" refers to any method known in the art for functionally connecting protein domains, including without limitation recombinant fusion with or without intervening domains, intein-mediated fusion, non-covalent association, and covalent bonding, including disulfide bonding; hydrogen bonding; electrostatic bonding; and conformational bonding, e.g., antibody-antigen, and biotin-avidin associations.

"Thermally stable polymerase" as used herein refers to any enzyme that catalyzes polynucleotide synthesis by addition of nucleotide units to a nucleotide chain using DNA or RNA as a template and has an optimal activity at a temperature above 45° C.

The term "amplification reaction" refers to any in vitro means for multiplying the copies of a target sequence of nucleic acid.

"Amplifying" refers to a step of submitting a solution to conditions sufficient to allow for amplification of a polynucleotide if all of the components of the reaction are intact. Components of an amplification reaction include, e.g., primers, a polynucleotide template, polymerase, nucleotides, and the like. The term "amplifying" typically refers to an "exponential" increase in target nucleic acid. However, "amplifying" as used herein can also refer to linear increases in the numbers of a select target sequence of nucleic acid.

The term "amplification reaction mixture" refers to an aqueous solution comprising the various reagents used to amplify a target nucleic acid. These include components such as enzymes, aqueous buffers, salts, amplification primers, target nucleic acid, and nucleoside triphosphates. Depending upon the context, the mixture can be either a complete or incomplete amplification reaction mixture "Polymerase chain reaction" or "PCR" refers to a method whereby a specific segment or subsequence of a target double-stranded DNA, is amplified in a geometric progression. PCR is well known to those of skill in the art; see, e.g., U.S. Pat. Nos. 4,683,195 and 4,683,202; and *PCR Protocols: A Guide to Methods and Applications*, Innis et al., eds, 1990; Sambrook and Russell, MOLECULAR CLONING, A LABORATORY MANUAL (3rd ed. 2001); and CURRENT PROTOCOLS IN MOLECULAR BIOLOGY (Ausubel et al., eds., John Wiley & Sons, Inc. 1994-1997, 2001 version).

A "primer" refers to a polynucleotide sequence that hybridizes to a sequence on a target nucleic acid template and serves as a point of initiation of nucleic acid synthesis. In the context of the invention, a primer is a component in an amplification reaction that participates in the amplification of the target nucleic acid. Primers can be of a variety of lengths and are often less than 50 nucleotides in length, for example 12-25 nucleotides, in length. The length and sequences of primers for use in PCR can be designed based on principles known to those of skill in the art, see, e.g., Innis et al., supra.

A "probe" refers to a polynucleotide sequence capable of hybridization to a target polynucleotide sequence of interest and allows for the specific detecting of the polynucleotide sequence of choice. For example, a "probe" can comprise a polynucleotide linked to fluorescent or quenching reagent, thereby allowing for the detection of these reagents.

A "mismatched nucleotide" or a "mismatch" refers to a nucleotide that is not complementary to the target sequence at that position.

The term "subsequence" refers to a sequence of nucleotides that are contiguous within a second sequence but does not include all of the nucleotides of the second sequence.

A "target" or "target nucleic acid sequence" refers to a single or double stranded polynucleotide sequence sought to be amplified in an amplification reaction. Two target sequences are different if they comprise non-identical polynucleotide sequences. The target nucleic acid sequence is typically amplified by a primer set in an amplification reaction.

A "temperature profile" refers to the temperature and lengths of time of the denaturation, annealing and/or extension steps of a PCR reaction. A temperature profile for a PCR reaction typically consists of 10 to 60 repetitions of similar or identical shorter temperature profiles; each of these shorter profiles typically define a two step or three-step PCR reaction. Selection of a "temperature profile" is based on various considerations known to those of skill in the art, see, e.g., Innis et al., supra. In a long PCR reaction as described herein, the extension time required to obtain an amplification product of 5 kb or greater in length is reduced compared to conventional polymerase mixtures.

Amplification or PCR "sensitivity" refers to the ability to amplify a target nucleic acid that is present in low copy number. "Low copy number" refers to $10^5$, often $10^4$, $10^3$, $10^2$, or fewer, copies of the target sequence in the nucleic acid sample to be amplified.

A "template" refers to a double stranded polynucleotide sequence that comprises the target polynucleotide to be amplified, flanked by primer hybridization sites. Thus, a "target template" comprises the target polynucleotide sequence and the flanking hybridization sites for a 5' primer and a 3' primer.

"Multiplex amplification" refers to amplification of multiple polynucleotide fragments in the same reaction (see, e.g., PCR PRIMER, A LABORATORY MANUAL (Dieffenbach, ed. 1995) Cold Spring Harbor Press, pages 157-171).

A "polymorphism" is an allelic variant. Polymorphisms can include single nucleotide polymorphisms as well as simple sequence length polymorphisms. A polymorphism can be due to one or more nucleotide substitutions at one allele in comparison to another allele or can be due to an insertion or deletion.

Introduction

Prior art techniques for performing quantitative amplification have not employed a 3'-labeled or dual-labeled hybridization probe and a reaction comprising an enzyme having 3' exonuclease activity. For example, in previous applications, an amplification product is first obtained and then quantified by measuring the amount of 3' label release from a probe hybridized to the amplified product (see, e.g., U.S. Pat. No. 6,653,078); or a 3'-labeled oligonucleotide queries a particular nucleotide and participates in the amplification (or primer extension) reaction as a primer (e.g., U.S. Pat. Nos. 5,391, 480; 6,248,526; U.S. Patent Application No. 20020142336). Here, the probe is included in the amplification reaction along with primers that amplify the template. Further, the probe does not query a particular nucleic acid position, it is typically designed to detect any nucleic acid sequence of interest. The polymerase, exonuclease, and probe components of the invention are described in further detail hereinbelow.

Polymerases Useful in the Invention

A variety of polymerases can be used in the methods of the invention. At least five families of DNA-dependent DNA polymerases are known, although most fall into families A, B and C. There is little or no structural or sequence similarity among the various families. Most family A polymerases are single chain proteins that can contain multiple enzymatic functions including polymerase, 3' to 5' exonuclease activity and 5' to 3' exonuclease activity. Family B polymerases typically have a single catalytic domain with polymerase and 3' to 5' exonuclease activity, as well as accessory factors. Family C polymerases are typically multi-subunit proteins with polymerizing and 3' to 5' exonuclease activity. In *E. coli*, three types of DNA polymerases have been found, DNA polymerases I (family A), II (family B), and III (family C). In eukaryotic cells, three different family B polymerases, DNA polymerases α, δ, and ε, are implicated in nuclear replication, and a family A polymerase, polymerase γ, is used for mitochondrial DNA replication. Other types of DNA polymerases include phage polymerases.

A proofreading polymerase is often used in this invention. As previously noted, a proofreading polymerase has the ability to catalyze the template-directed synthesis of DNA from deoxyribonucleotide triphosphates, and also a 3' to 5' proofreading exonuclease activity and thus can excise a mismatched nucleotide at or near the 3' terminus of an oligonucleotide when it is hybridized to the target sequence. Proofreading enzymes are typically B-type polymerases. Thermostable B-type polymerase are particularly useful in cycling reactions, these include *Pyrococcus* polymerases e.g., Pfu, Pwo, Pho, Pab, Pko, Pgl polymerases; *Thermococcus* polymerases, e.g., *Thermococcus litoralis, Thermococus barossii*, and *Thermococcus gorgonarius* polymerases; and polymerases from *Pyrodictium* sp. Thermostable polymerases having 3' to 5' exonuclease activity can also be isolated from eubacterial strains such as *Thermotoga*.

A-type polymerases can also be used in the reactions, either alone or in conjunction with another polymerase, e.g., a polymerase having 3' to 5' exonuclease activity. An A-type polymerase for use in this invention often lacks, or is otherwise deficient in, 5' to 3' exonuclease activity. For example, an N-terminal deletion mutant of Taq polymerase in which the 5' to 3' exonuclease activity is deleted (ΔTaq) can be used. As appreciated by one of skill in the art, Taq polymerase also lacks 3' to 5' error-correcting activity; accordingly, a reaction of the invention employing this mutant Taq would also comprise a polymerase having error-correcting activity or another molecule that has 3' to 5' exonuclease activity.

Further, in some embodiments, non-thermostable polymerases are useful. For example, the large fragment of *E. coli* DNA Polymerase I (Klenow) has 3' to 5' exonuclease activity and lacks 5' to 3' exonclease activity. This enzyme or equivalent enzymes can be used in embodiments where the amplification reaction is not performed at high temperatures.

The polymerase and/or 3' to 5' exonuclease may be a hybrid protein. The term "hybrid protein" is used herein to describe a protein that comprises amino acid residues from multiple parent sequences. Examples of hybrid polymerase proteins and methods of generating hybrid proteins are disclosed in WO2004011605. Such polymerases are therefore non-naturally occurring variants of polymerases.

In some embodiments, the polymerase that provides the elongation activity may comprise a mutated exonuclease domain e.g., such as a hybrid polymerase, that lacks substantial 3' to 5' exonuclease activity. Such an enzyme has reduced exonuclease activity in comparison to a parent polymerase exonuclease domain.

In some embodiments, it is advantageous to use polymerases having enhanced processivity, "improved polymerases". Examples of these include those described in WO01/92501 and co-pending U.S. application Ser. No. 10/280,139. These improved polymerases exhibit enhanced processivity due to the presence of a sequence-non-specific double-stranded DNA binding domain that is joined to the polymerase or the enzymatic domain of the polymerase). Often the binding domain is from a thermostable organism and provides enhanced activity at higher temperatures, e.g., temperatures above 45° C. For example, Sso7d and Sac7d are small (about 7,000 kd MW), basic chromosomal proteins from the hyperthermophilic archaeabacteria *Sulfolobus solfataricus* and *S. acidocaldarius*, respectively (see, e.g., Choli et al., *Biochimica et Biophysica Acta* 950:193-203, 1988; Baumann et al., *Structural Biol.* 1:808-819, 1994; and Gao et al, *Nature Struc. Biol.* 5:782-786, 1998). These proteins bind DNA in a sequence-independent manner and when bound, increase the $T_M$ of DNA by up to 40° C. under some conditions (McAfee et al., *Biochemistry* 34:10063-10077, 1995). These proteins and their homologs are often used as the sequence-non-specific DNA binding domain in improved polymerase fusion proteins. Sso7d, Sac7d, Sac7e and related sequences (referred to herein as "Sso7 sequences" or "Sso7 domains") are known in the art (see, e.g., accession numbers (P39476 (Sso7d); P13123 (Sac7d); and P13125 (Sac7e)). These sequences typically have at least 75% or greater, of 80%, 85%, 90%, or 95% or greater, amino acid sequence identity. For example, an Sso7 protein typically has at least 75% identity to an Sso7d sequence.

Other sequence non-specific double-stranded nucleic acid binding proteins are topoisomerase, helicase, or PCNA. Additional examples are described in Motz et al., *J Biol. Chem.* 277:16179-88, 2002; Pavlov et al, *Proc. Natl. Acad. Sci. USA* 99:13510-13515, 2002).

Mixtures of polymerases may also be used in some applications in order to enhance particular aspects of the reaction, such as the ability to synthesize long fragments. For example, a mutant Taq lacking 5' to 3' exonuclease activity can be used with an error-correcting polymerase.

Enzymes Having Exonuclease Activity

The invention employs an enzyme having 3' to 5' exonucleolytic activity. Further, in typical embodiments, the 3' to 5' exonuclease is a proofreading activity (typically from a proofreading polymerase) that preferentially cleaves a 3' mismatched nucleotide, i.e., has the ability to differentially excise a matched or mismatched nucleotide at the 3' terminus of an oligonucleotide, when hybridized to the target DNA. The 3' to 5' exonuclease activity can be provided by polymerases, e.g., a proofreading polymerase, or other exonuclease molecules. Suitable enzymes include proofreading DNA polymerases, described above, and exonuclease III of *E. coli* and similar enzymes isolated from other organisms.

Exonuclease III catalyzes the stepwise removal of mononucleotides from 3'-hydroxyl termini of duplex DNA. The preferred substrates are blunt or recessed 3'-termini, although the enzyme also acts at nicks and duplex DNA to produce single-strand gaps. The enzyme is not active on single-stranded DNA, and thus 3'-protruding termini are resistant to cleavage. The degree of resistance depends on the length of the extension, with extensions 4 bases or longer being essentially resistant to cleavage.

It is advantageous if the exonuclease activity is thermostable. For example, EP-A-1088891 discloses a thermostable enzyme from *Archaeolgobus fulgidus* that catalyzes the degradation of mismatched ends of primers or polynucleotide in the 3' to 5' direction in double stranded DNA. Related enzymes can also be obtained from other *Archae* species as well as thermophilic eubacteria.

In some embodiments, the exonuclease activity can be supplied by a proofreading DNA polymerase molecule that has an inactive polymerase domain or a polymerase domain that has one or more mutations resulting in substantially reduced activity of the polymerase domain in comparison to the activity of the starting polymerase domain. Such a protein is often referred to herein as pol⁻exo⁺. In this circumstance, the polymerase activity in the amplification reaction mixture is predominantly provided by a different polymerase molecule that has an active polymerase domain. Examples of polymerase polypeptides that have deficient polymerase activity, but retain exonuclease activity, and methods of generating additional such molecules are provided, e.g., in WO2004011605.

A polymerase having substantially reduced polymerase activity refers to a polymerase that generally has less than 20% polymerase activity, i.e., elongation activity, and most often less than 10% elongation activity, in comparison to a parent enzyme. Thus, the elongation activity contributed by a pol⁻exo⁺ protein present in an amplification reaction of the invention represents less than 10%, usually less than 5%, or 1%, of the elongation activity in the reaction. For example, in an amplification reaction of the invention that comprises a polymerase and a pol⁻exo⁺ protein (to provide the exonuclease activity) in which the total elongation polymerase activity is 20 U/ml; then the elongation activity from the pol⁻exo⁺ protein is usually 2 U/ml, 1 U/ml, 0.2 U/ml or less of the total elongation activity. Illustrative polymerase sequences that have little or no polymerase elongation activity, but retain exonuclease activity (pol⁻exo⁺) are provided in SEQ ID NOs 2 and 4.

In some embodiments, an exonuclease activity for use in the invention preferably has exhibits greater exonuclease activity towards a double-stranded ($exo^{ds}$) nucleic acid molecule in comparison to its exonuclease activity towards a singled-stranded ($exo^{ss}$) nucleic acid. The ratio of $exo^{ds}$ to $exo^{ss}$ is used to compare two enzymes. The enzyme that has the higher ratio using the same substrates is often better for use in this invention. The activity towards ds versus ss nucleic acid substrates can be measured. For example, an assay can be used to measure the exo activity of an exonuclease towards a given probe in a double stranded form relative to that towards the same probe in the single stranded form.

Different family B polymerases can result in different $exo^{ds}/exo^{ss}$ ratios with the same probe. In some embodiments, a polymerases that has a higher $exo^{ds}/exo^{ss}$ ratio in comparison to the other polymerase can perform better, i.e., is more sensitive and generates less background than a polymerase that has a lower $exo^{ds}/exo^{ss}$. An exemplary assay to determine the ratio of exonuclease activity towards a double-stranded nucleic acid substrate to exonuclease activity towards a single-stranded nucleic acid substrate is provided in the Examples section. As used herein, exonuclease activity towards a double-stranded nucleic acid substrate is sometimes referred to as "double-stranded" exonuclease activity while the activity towards a single-stranded nucleic acid is substrate is referred to as "single-stranded" exonuclease activity. The double-stranded exonuclease activity is also referred to as the exonuclease proofreading ($exo^{Pfr}$) activity, i.e., the 3' nucleotide is mismatched to the target sequence.

Hot Start Amplification Reactions

In some embodiments, it is beneficial to employ "hot start" methods to decrease the generation of primer dimers and unspecific amplification products at ambient temperature. A number of hot-start methods are known. These include physical separation of the polymerase, use of nucleic acid additives to inhibit extension reactions at low temperatures, and modifications to the active site of the polymerase. Often, it may be desirable to use "hot start" polymerases. In a hot-start polymerase, a molecule is typically bound to the enzyme at the active site. The molecule is removed at high temperatures (e.g., at 95° C.). The molecule can be an antibody, peptide, or a small organic molecule. For example, hot-start can be achieved using an antibody that binds to a polymerase with high affinity at ambient temperatures in an inhibitory manner. The complex is dissociated in a high temperature preheating step.

A polymerase can also be chemically modified for hot-start. Heat labile blocking groups are introduced into the Polymerase, which render the enzyme inactive at room temperature. These blocking groups are removed at high temperature prior to cycling such that the enzyme is activated. Heat labile modifications include coupling citraconic anhydride or aconitric anhydride to lysine residues of the enzyme (e.g., U.S. Pat. No. 5,677,152).

U.S. patent application no. 20030119150 also discloses a concept of hot start PCR that employs a thermostable exonuclease and a polymerase. This method is based on preventing primer elongation at low temperatures by introducing chemical modifications at the 3' end of at least one primer. A thermostable exonuclease is used that is inactive at ambient temperatures or below. Upon temperature increase, the exonuclease becomes active and capable of removing the 3' modification of the primer to enable it to participate in the amplification reaction. U.S. patent application 20030119150 further teaches that when hybridization probes are used for realtime monitoring, e.g., TaqMan hybridization probes, Molecular Beacon oligonjucleotides, or two oligonucletide hybridization methods, the presence of a thermostable exonuclease III requires a suitable blocking method for the 3' end of the detection probe to avoid 3' digestion.

Oligonucleotide Probes and Polymerase Reactions

Oligonucleotide primers and probes can be prepared using any suitable method, such as, for example, methods using phosphotriesters and phosphodiesters well known to those skilled in the art. In some embodiments, one or more phosporothioate linkages may be included in the probe. The oligonucleotide can also be modified at the base moiety, sugar moiety, or phosphate backbone with minor groove binders (further discussed below), intercalating agents an the like.

The primers for the amplification reactions are designed according to known algorithms. The primers are designed to hybridize to sequences that flank the target nucleic acid. Typically, commercially available or custom software will use algorithms to design primers such that the annealing temperatures are close to melting temperature. Amplification primers are usually at least 12 bases, more often about 15, 18, or 20 bases in length. Primers are typically designed so that all primers participating in a particular reaction have melting temperatures that are within 5° C., and most preferably within 2° C. of each other. Primers are further designed to avoid priming on themselves or each other. Primer concentration should be sufficient to bind to the amount of target sequences that are amplified so as to provide an accurate assessment of the quantity of amplified sequence. Those of skill in the art will recognize that the amount of concentration of primer will vary according to the binding affinity of the primers as well as the quantity of sequence to be bound. Typical primer concentrations will range from 0.01 µM to 1.0 µM.

The polymerase reactions are incubated under conditions in which the primers hybridize to the target sequence template and are extended by a polymerase. As appreciated by those of skill in the art, such reaction conditions may vary, depending on the target nucleic acid of interest and the composition of the primer. The amplification reaction cycle conditions are selected so that the primers hybridize specifically to the target template sequence and are extended. Primers that hybridize specifically to a target template amplify the target sequence preferentially in comparison to other nucleic acids that may be present in the sample that is analyzed. Exemplary PCR conditions for particular primer sets are provided in the examples.

Hybridization Probes

The probe oligonucleotides for use in the invention can be any suitable size, and are often in the range of from about 6 to about 100 nucleotides, more often from about 6 to about 80 nucleotides and frequently from about 10 to about 40 nucleotides. The precise sequence and length of an oligonucleotide probe depends in part on the nature of the target polynucleotide to which it binds. The binding location and length may be varied to achieve appropriate annealing and melting properties for a particular embodiment. Guidance for making such design choices can be found in many art recognized references. Hybridization of the probe, in conjunction with amplification of the target sequence with primers to amplify the template, provides a quantitative determination of the amount of the target nucleic acid sequence in a sample.

In some embodiments, it can be desirable to design probes taking into consideration the following. There are several scenarios that could generate non-specific signals in the amplification methods of the invention. For example, if the 3'-end of the probe anneals or partially anneals to the 3'-end of one of the primers, e.g., the reverse primer, leaving the 3' nucleotide of the probe as a mismatch, the polymerase enzyme may potentially recognize this as a substrate and cleave the probe. The cleaved probe would then have an exposed 3'-end hydroxyl group, which would allow it to serve as a primer. The probe-turned into primer in this example could be extended on the reverse primer. In the next cycle, the extended probe-turned into primer could serve as the template for the reverse primer and be copied. Thus, a generated duplex could have all the sequence generated from the probe and the reverse primer, but not the template, primer dimer. It may therefore be desirable to design probes that do not have this problem. This can be achieved based on sequence information; further, probes can be designed to incorporate an abasic site in the probe.

As understood by those in the art, an abasic site lacks a base at a position in the oligonucleotide probe, i.e., the sugar residue is present at the position in the probe, but there is no base. Oligonucleotide probes having an abasic site are typically synthesized with the abasic site and are commercially available (e.g., Integrated DNA Technologies, Inc., "IDT"). Thus, in FIG. 10, for example, the position in the probe sequence is designated as "0". An abasic site present in the probe does not prevent the probe from being cleaved, or from being extended, but it prevents the reverse primer from being extended to its end in the following cycle. The end result is that no exponential amplification of the undesired products occurs. An abasic site is typically included at an internal position of the probe. The position is selected so that it does not destabilize binding of the probe to the target nucleic acid. For example, an abasic site may be positioned in the middle third of the probe sequence. In other embodiments, the abasic site is positioned at least 3 nucleotides from the 3' end of the probe; or positioned towards the 5' end of the probe, e.g., 3 nucleotides from the 5' end.

In some embodiments, the hybridization probes contain one or more mismatched nucleotide at the 3' end of the molecule. Thus, a probe typically has at least one mismatch at the 3' end, but can also have two, three, four, five, six, or seven, or more mismatched nucleotides. In some embodiments, it is desirable to design a probe mismatched sequence such that the sequence will form a stem-loop structure where the extra mismatched bases can fold back to form base pairs with the 5' region of the probe. This can, e.g., minimize the hydrolysis of the probe by the exonuclease before hybridization to the target occurs.

As appreciated by one in the art, probes can be evaluated for sensitivity and specificity as explained in the examples section below. In many real-time methods of the invention, a 3' mismatched nucleotide is designed to detect the presence of any target nucleic acid present in the sample, i.e., the probe is designed so that the mismatched residue is at an invariant, rather than polymorphic, nucleotide in the target nucleic acid.

A probe for use in the invention is labeled with at least one detectable moiety. The detectable moiety can be at the 3' end of the probe. It can also be desirable to position a detectable moiety at an internal nucleotide, e.g., a label may be at an internal nucleotide rather than the 3' end of the probe. Where the label is on the 3' terminal nucleotide of the probe, the label can be positioned either on the base, or on the backbone. In some embodiments, it may be desirable to position a 3' terminal label on the backbone, e.g., to serve as a partial "block" to exonuclease activity that targets the single-stranded substrate.

In some embodiments, it may be desirable to design a probe that has a particular sequence on the 3' end. For example, the 3' to 5' exonuclease may be preferentially active towards one or more particular sequences. Accordingly, the probe is designed to hybridize to a region of the target nucleic acid sequence that comprises a sequence that is complementary to the particular sequence that the practitioner wishes to position at the 3' end of the probe. For example, in some embodiments, a 3' to 5' exonuclease may exhibit preferential activity towards a TCAGC sequence adjacent to the 3' nucleotide where the 3' nucleotide is a mismatch to the template sequence, i.e, the sequence at the 3' end of the probe is TAGCN, where N is a mismatch to the target nucleic acid. Thus, a sequence in the target nucleic acid that includes the complement to the TCAGC that will be present in the probe will preferably be selected as the target region to which the probe binds.

In some embodiments, a "variant" of a sequence such as a TCAGCN sequence may be employed, e.g. TCAACN, TCACCN, or TCAGGN. In additional embodiments, one or more positions in TCAGC are replaced, e.g., one to three positions, by nucleotides that mismatch the target sequence.

For example, a probe may be designed to have a 3' end that is TCANNN or TCAGNN (where N designates a mismatch to the target nucleic acid).

The hybridization probe may be extended during the course of the amplification upon cleavage of the 3' nucleotide. However, the hybridization probe is not an amplification primer as described herein. The hybridization probe binds to a region that is flanked by the sequences to which the amplification primers bind.

Labels

The hybridization probe is typically labeled with a detectable moiety. The detectable moiety can be any moiety that directly or indirectly results in a change in signal when it is cleaved.

Typically, the hybridization probe is labeled with a fluorescent molecule. Examples of fluorescence labels include, but are not limited to: Alexa Fluor dyes (Alexa Fluor 350, Alexa Fluor 488, Alexa Fluor 532, Alexa Fluor 546, Alexa Fluor 568, Alexa Fluor 594, Alexa Fluor 633, Alexa Fluor 660 and Alexa Fluor 680), AMCA, AMCA-S, BODIPY dyes (BODIPY FL, BODIPY R6G, BODIPY TMR, BODIPY TR, BODIPY 530/550, BODIPY 558/568, BODIPY 564/570, BODIPY 576/589, BODIPY 581/591, BODIPY 630/650, BODIPY 650/665), Carboxyrhodamine 6G, carboxy-X-rhodamine (ROX), Cascade Blue, Cascade Yellow, Cyanine dyes (Cy3, Cy5, Cy3.5, Cy5.5), Dansyl, Dapoxyl, Dialkylaminocoumarin, 4',5'-Dichloro-2',7'-dimethoxy-fluorescein, DM-NERF, Eosin, Erythrosin, Fluorescein, FAM, Hydroxycoumarin, IRDyes (IRD40, IRD 700, IRD 800), JOE, Lissamine rhodamine B, Marina Blue, Methoxycoumarin, Naphthofluorescein, Oregon Green 488, Oregon Green 500, Oregon Green 514, Pacific Blue, PyMPO, Pyrene, Rhodamine 6G, Rhodamine Green, Rhodamine Red, Rhodol Green, 2',4',5',7'-Tetra-bromosulfone-fluorescein, Tetramethyl-rhodamine (TMR), Carboxytetramethylrhodamine (TAMRA), Texas Red, and Texas Red-X.

Often, the fluorescent label is employed in conjunction with a second label in the molecule that interacts with it. Thus, fluorescence-based assays can also rely for signal generation on fluorescence resonance energy transfer, or "FRET", according to which a change in fluorescence is caused by a change in the distance separating a first fluorophore from an interacting resonance energy acceptor, either another fluorophore or a quencher. Combinations of a fluorophore and an interacting molecule or moiety, including quenching molecules or moieties, are known as "FRET pairs." The mechanism of FRET-pair interaction requires that the absorption spectrum of one member of the pair overlaps the emission spectrum of the other member, the first fluorophore. If the interacting molecule or moiety is a quencher, its absorption spectrum must overlap the emission spectrum of the fluorophore. Stryer, L., *Ann. Rev. Biochem.* 47: 819-846 (1978); BIOPHYSICAL CHEMISTRY part II, Techniques for the Study of Biological Structure and Function, C. R. Cantor and P. R. Schimmel, pages 448-455 (W.H. Freeman and Co., San Francisco, U.S.A., 1980); and Selvin, P. R., *Methods in Enzymology* 246: 300-335 (1995). Efficient FRET interaction requires that the absorption and emission spectra of the pair have a large degree of overlap. The efficiency of FRET interaction is linearly proportional to that overlap. See Haugland, R. P. et al. *Proc. Natl. Acad. Sci. USA* 63: 24-30 (1969). Typically, a large magnitude of signal (i.e., a high degree of overlap) is required. FRET pairs, including fluorophore-quencher pairs, are therefore typically chosen on that basis.

A quencher includes any moiety that is capable of absorbing the energy of an excited fluorescent label when located in close proximity to the fluorescent label and capable of dissipating that energy without the emission of visible light. Examples of quenchers include, but are not limited to, DABCYL (4-(4'-dimethylaminophenylazo) benzoic acid) succinimidyl ester, diarylrhodamine carboxylic acid, succinimidyl ester (QSY-7), and 4',5'-dinitrofluorescein carboxylic acid, succinimidyl ester (QSY-33) (all available from Molecular Probes), quencher1 (Q1; available from Epoch), or Iowa Black™ quenchers (Integrated DNA Technologies), and "Black hole quenchers" BHQ-1, BHQ-2, and BHQ-3 (available form BioSearch, Inc.).

The second label in dual-labeled probes may be present at the 5' end, but it need not be. For example, a quencher moiety may be at least 1, 2, 3, 4, 5, 6, 7, 8, 9, 10, or more nucleotides away from the fluorophore label, so long as the distance allows the two labels to interact when the probe is hybridized to the target.

Base-linked fluors and quenchers are well-known in the art. They can be obtained, for example, from Life Technologies (Gaithersburg, Md.), Sigma-Genosys (The Woodlands, Tex.), Genset Corp. (La Jolla, Calif.), or Synthetic Genetics (San Diego, Calif.). In some cases, base-linked fluors are incorporated into the oligonucleotides by post-synthesis modification of oligonucleotides that were synthesized with reactive groups linked to bases. The fluor can be attached to the 3' OH of the sugar or the base.

Practical guidance is readily available in the literature for selecting appropriate donor-acceptor pairs for particular probes, as exemplified by the following references: Pesce et al., Eds., Fluorescence Spectroscopy (Marcel Dekker, New York, 1971); White et al., Fluorescence Analysis: A Practical Approach (Marcel Dekker, New York, 1970). The literature also includes references providing exhaustive lists of fluorescent and chromogenic molecules and their relevant optical properties for choosing reporter-quencher pairs (see, for example, Berlman, Handbook of Fluorescence Spectra of Aromatic Molecules, 2nd Edition (Academic Press, New York, 1971); Griffiths, Colour and Constitution of Organic Molecules (Academic Press, New York, 1976); Bishop, Ed., Indicators (Pergamon Press, Oxford, 1972); Haugland, Handbook of Fluorescent Probes and Research Chemicals (Molecular Probes, Eugene, 1992) Pringsheim, Fluorescence and Phosphorescence (Interscience Publishers, New York, 1949). Further, the literature provides ample guidance for derivatizing reporter and quencher molecules for covalent attachment via common reactive groups that can be added to an oligonucleotide (see, e.g., Haugland (supra); U.S. Pat. Nos. 3,996,345; and 4,351,760).

Other fluorescent-labeled probes that can be used in the invention do not contain a quencher moiety. Such fluorescent oligonucleotide probes are designed to self-quench based on sequence context. These probes (LUX™ probes) quench when free in solution, fluoresce weakly when denatured, and emit light strongly when incorporated into DNA.

As appreciated by those in the art, other energy donor and energy acceptor molecules based on energy transfer mechanisms other than fluorescence can also be used in practicing this invention. The include donor/acceptor pairs such as radioisotope/scintillant, nmr sensitive nuclei/unpaired electrons and the like.

Ct Determination

In typical applications, the amount of cleavage product generated by the 3' exonuclease activity during the reaction is determined based on cycle threshold (Ct) value, which represents the number of cycles required to generate a detectable amount of DNA. Determination of Ct values is well known in the art. Briefly, during PCR, as the amount of formed amplicon increases, the signal intensity increases to a measurable level and reaches a plateau in later cycles when the reaction enters into a non-logarithmic phase. By plotting signal intensity versus the cycle number during the logrithmic phase of the reaction, the specific cycle at which a measurable signal is obtained can be deduced and used to calculate the quantity of the target before the start of the PCR. Exemplary methods of determining Ct are described in, e.g., Heid et al. *Genome Methods* 6:986-94, 1996, with reference to hydrolysis probes.

Additional Probe Components

The probe can also comprise additional components. These include minor groove binding proteins and/or a modified base DNA probes with conjugated minor groove binder (MGB) groups form extremely stable duplexes with single-stranded DNA targets, allowing shorter probes to be used for hybridization based assays (e.g., U.S. Pat. No. 5,801,155). Accordingly, in some embodiments, minor groove binder groups are also included in the probe, e.g., at the 5' end of the probe. A variety of suitable minor groove binders have been described in the literature. See, for example, U.S. Pat. No. 5,801,155; Wemmer & Dervan, *Current Opinon in Structural Biology* 7:355-361-(1997); Walker, et al., *Biopolymers* 44:323-334 (1997); Zimmer & Wahnert, *Prog. Biophys. Molec. Bio.* 47:31-112 (1986); and Reddy, et al., *Pharmacol. Therap.* 84:1-111 (1999). Suitable methods for attaching MGBs (as well as other moieties) through linkers to oligonucleotides are described in, for example, U.S. Pat. Nos. 5,512,677; 5,419,966; 5,696,251; 5,585,481; 5,942,610 and 5,736,626.

Multiplex Reactions

An amplification reaction of the invention can also be conducted under multiplex reactions conditions. A multiplex reaction can detect the presence of multiple target nucleic acid sequences using multiple hybridization probes. Each probe is labeled with a different label, e.g., fluorophor, to provide a distinct signal.

EXAMPLES

These examples show that a proofreading DNA polymerase can be used in a real-time qPCR reaction.

Example 1

Quantitative PCR Using a Polymerase Having Proofreading Activity and a Dual-Labeled Probe The proofreading DNA polymerase, Phusion™, a *Pyrococcus* polymerase with a processivity enhancing domain, was used in real-time qPCR reactions with a dual-labeled probe. This assay was compared to assays using a TaqMan™ probe. The probes are shown below. The probes are labeled with a fluorescence dye (Cy5) at the 5' end and a quencher (BHQ-2) at the 3' end. The probe used in the proofreading assay has a mismatched 3' nucleotide. It also has a phosphorothioate linkage between the last 2 bases, although inclusion of such a linkage is optional.
TaqMan™ Probe: 5Cy5/CAAGCTTCCCGTTCTCAGCC/3BHQ2 (SEQ ID NO:20)
Proofreading assay Probe: 5Cy5/CAAGCTTCCCGTTCTCAGC*G/3BHQ2 (SEQ ID NO:21)

Figure 2:
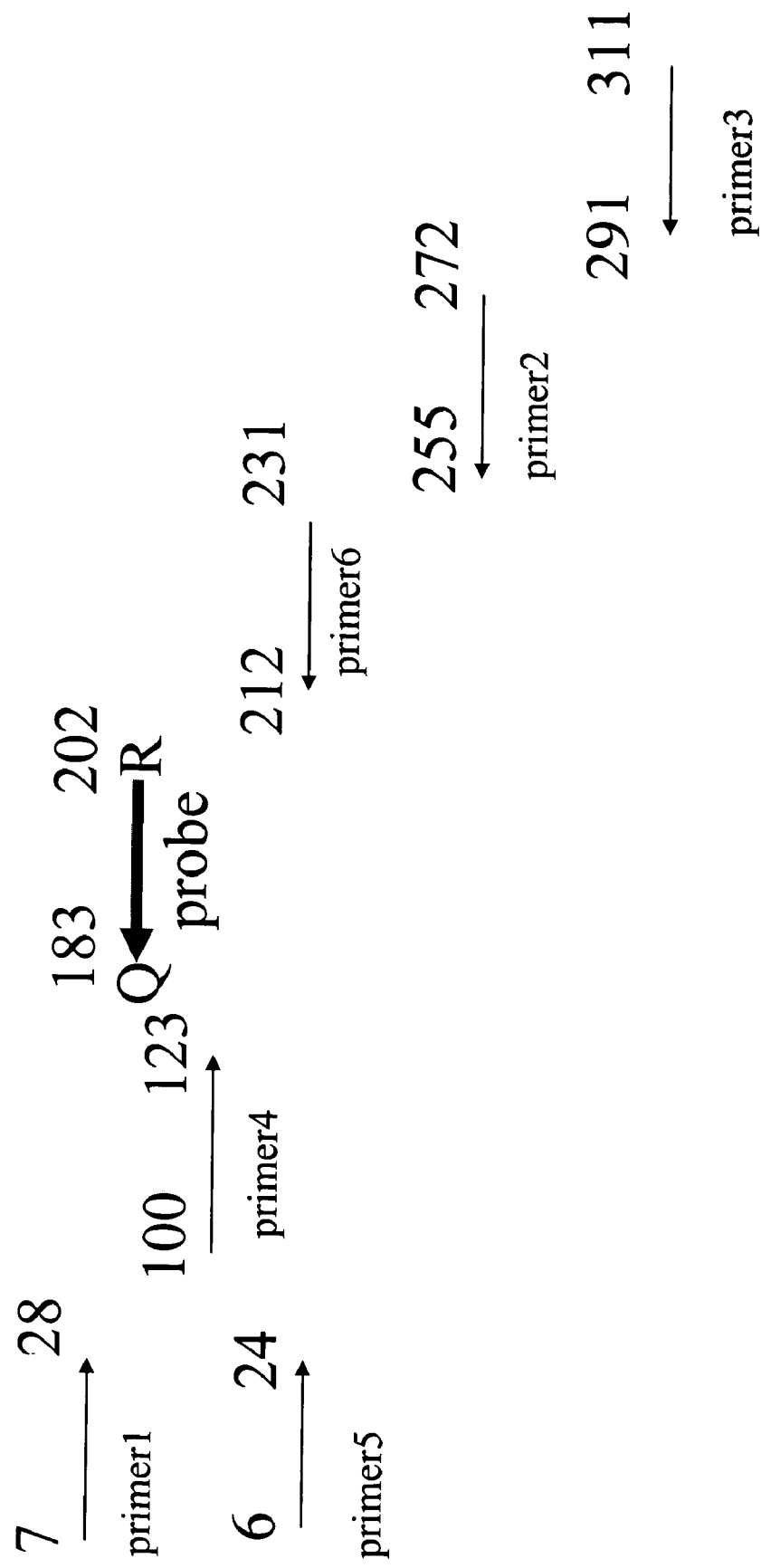
FIG. 2 shows the positions of the primers and probe in an exemplary quantitative PCR.

The probes were in qPCR reactions using a glyceraldehyde 3-phosphate dehydrogenase (GAPDH) template. The primers used in the PCR reactions and the relative position of the probe is shown in FIG. 2.

Figure 3:
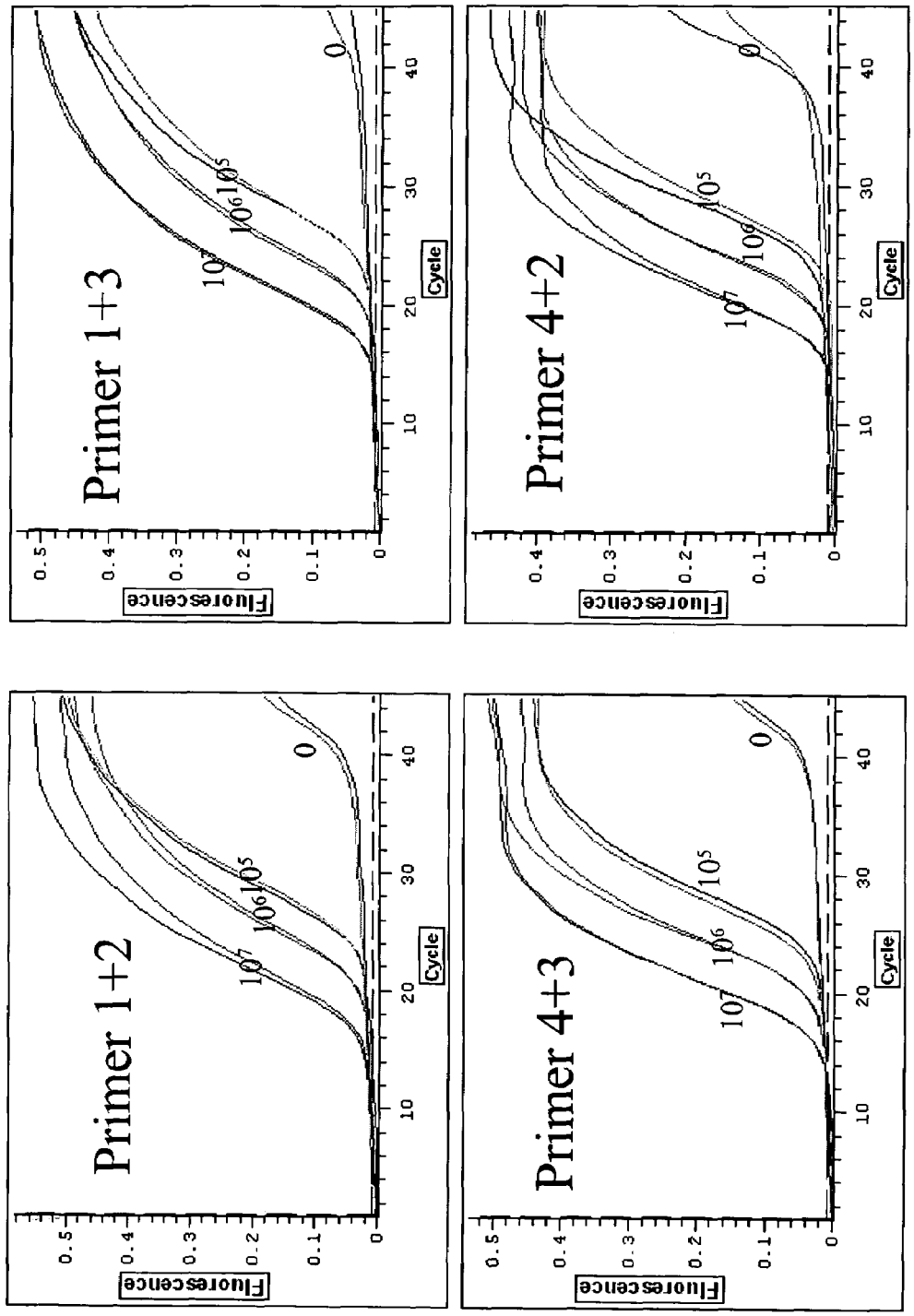
FIG. 3 shows the results of a quantitative PCR using a dual-labeled probe and an proofreading enzyme.
Figure 4:
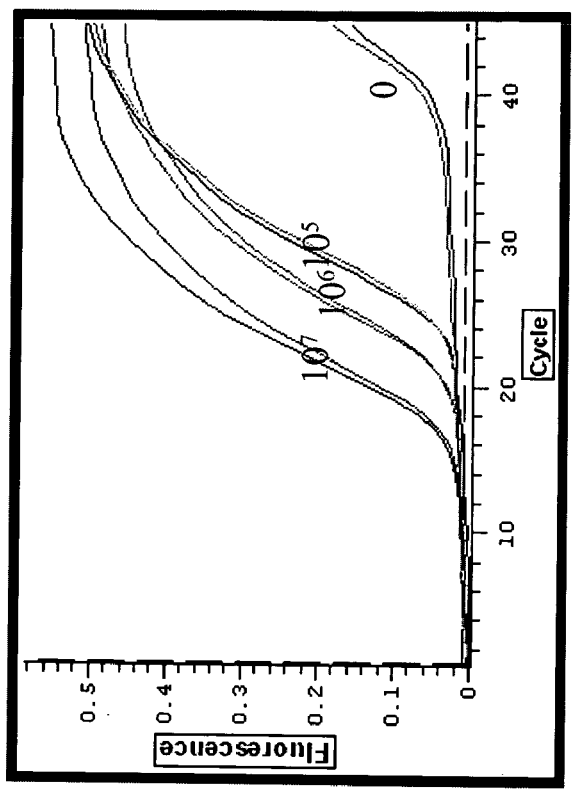
FIG. 4 shows a comparison of a quantitative PCR of the invention and a TaqMan™ assay.
Figure 4:
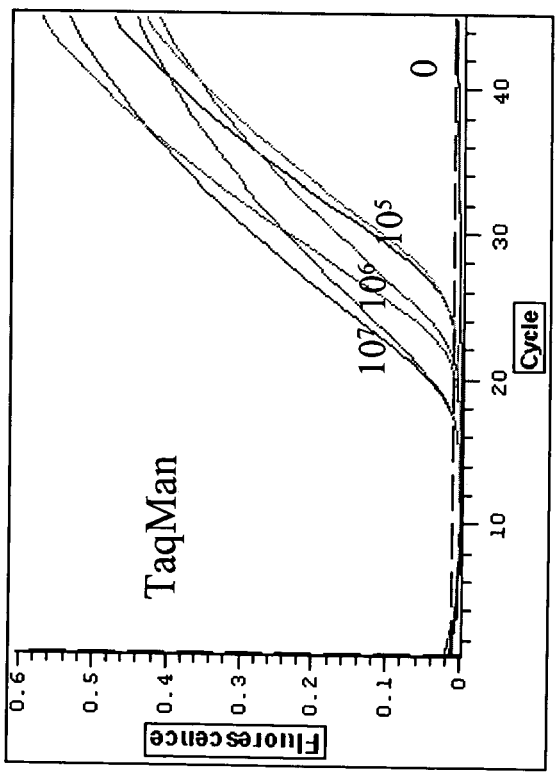

PCR amplification reaction mixtures contained the following:
Proofreading PCR with Phusion:
1× Phusion buffer A
0.2 mM dNTP
20 U/ml Phusion
0.3 µM Forward primer
0.3 µM Reverse primer
0.3 µM dual-labeled probe
$10^7$, $10^6$, $10^5$, or 0-copy pGAPDH template The reaction conditions were:
pseudo hot-start
98° C. 30 s
45× (98° C. 10 s, 60° C. 30 s, read, 72° C. 15 s)
72° C. 10 min TaqMan qPCR:
1× Universal PCR Master Mix
0.3 µM primer 5
0.3 µM primer 6
0.3 µM dual-labeled probe
$10^7$, $10^6$, $10^5$, or 0-copy pGAPDH template The reaction conditions were:
95° C. 10 min
45× (95° C. 15 s, 60° C. 1 min, read)
72° C. 10 min The ability of the proofreading probe to detect $10^7$, $10^6$, and $10^5$ copies of template using various primers sets is shown in FIG. 3. A comparison to a TaqMan™ qPCR using primers 5 and 6 is shown in FIG. 4. The results show that the fluorescence signals and Ct's were comparable in the TaqMan™ and proofreading assays.

Example 2

Quantitative PCR Using a Dual-Labeled Probe and Separating the Polymerase and Exonuclease Activity This example provides an illustration of a reaction in which the polymerase and 3' to 5' exonuclease activities are provided by separate proteins.

Figure 5:
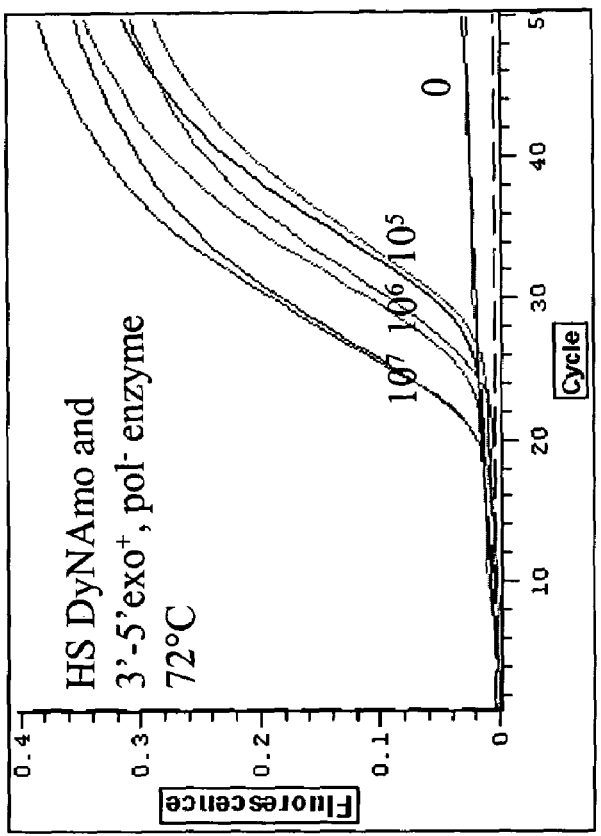
FIG. 5 shows the results of a reaction performed using separate DNA polymerase activity and 3' to 5' exonuclease activity.
Figure 5:
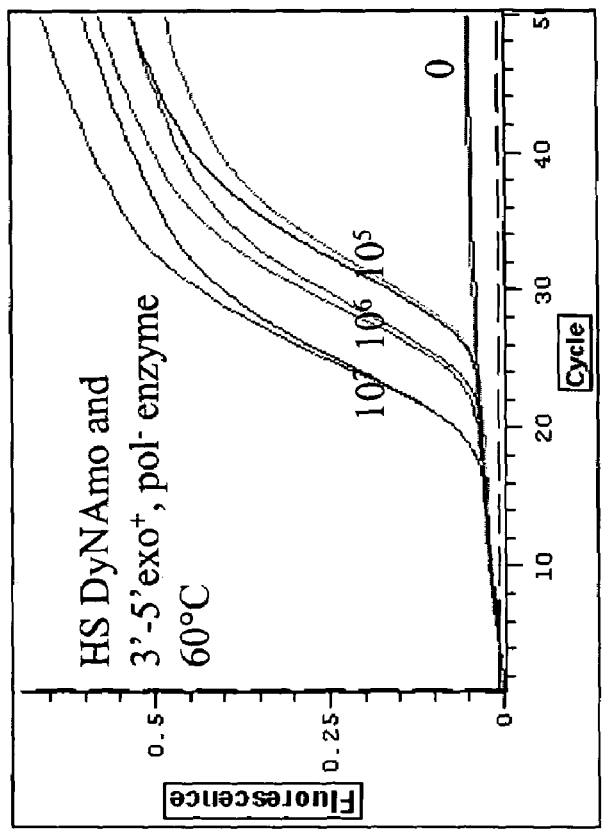
Figure 6:
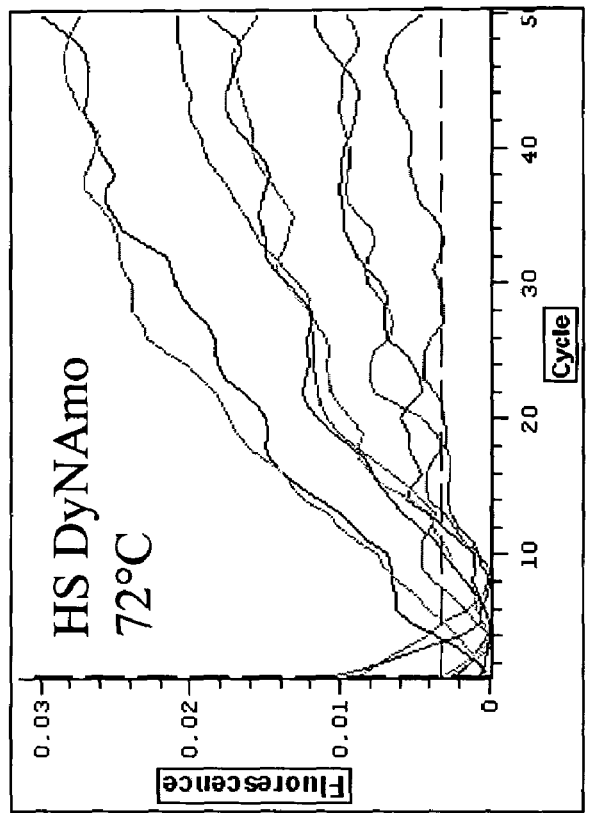
FIG. 6 shows a comparison of a PCR reaction using only HS DyNAmo.
Figure 6:
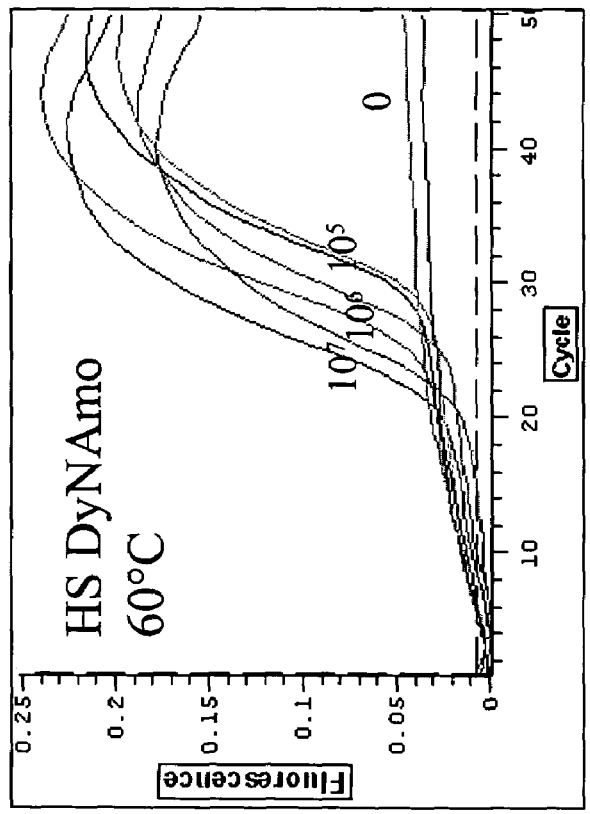

PCR was performed using a hot start DNA polymerase (HS DyNAmo) that lacks 5' to 3' exonuclease activity. The 3' to 5' exonuclease activity is provided by a hybrid polymerase (having a Pfu polymerase as one of the parents) where the hybrid polymerase substantially lacks polymerase activity (an exo⁺ pol⁻ polymerase). The reaction contained the following:
1× HS DyNAmo mix
112 U/ml exo+ pol– enzyme
0.3 µM forward primer
0.3 µM reverse primer
0.3 µM dual-labeled probe
$10^7$, $10^6$, $10^5$, or 0-copy pGAPDH template The reaction conditions were:
1. 95° C. 10 min
2. 95° C. 15 s
3. 60° C. 30 sec
4. read
5. 72° C. 30 sec
6. read
7. go to 2 for 49 times
8. 72° C. 10 min The results (FIG. 5) show that in the two-enzyme (HS DyNAmo and a 3' to 5' exo⁺, pol⁻ enzyme) PCR amplification reactions, non-specific signals were eliminated (note the 0-copy reactions). The dual-labeled probe was cleaved and fluorescence signals can be detected at both 60° C. and 72° C. For comparison (FIG. 6), in PCRs performed using only HS DyNAmo, low-level fluorescence signals can be detected at 60° C. due to the de-quenching of the probe upon hybridization, but no fluorescence signals are detected at 72° C.

Example 3

Quantitative qPCR Using a Probe with a Preferential Subsequence at the 3' End

To test whether there was any probe sequence preference exhibited by the 3' to 5' exonuclease activity, probes having different 3' ends were tested in qPCR reactions of the invention. The exonuclease activity in this example was an exo$^+$ pol$^-$ enzyme, such as that employed in Example 2. First, a 3' to 5' exonuclease assay was used to test 3' to 5' exonuclease activity toward probes with different 3' endings. The results indicated that the sequence of the last 10 bases, e.g., the last 5 bases, of the probe affected the 3' to 5' exonuclease activity of the exo$^+$pol$^-$ enzyme. The results demonstrated that probes having a 3' end sequence (before the mismatch) of TCAGC had the highest exo activity and provided improved performance in qPCR reactions of the invention in comparison to the other sequence. As there are 1024 possible sequences for a 5-base DNA element, additional sequences may also provide improved performance parameters in a qPCR reaction. Examples of probes designed having a TCAGC before the 3' end nucleotide that is a mismatch to the template are provided in FIG. 7. The probes are to the following target sequences: GUSB: beta glucuronidase; PGK: phosphoglycerate kinase I; TFRC: transferrrin receptor; RPLP: large ribosomal protein; GAPD: glyceraldehydes 3-phosphate dehydrogenase.

Thus, probes may be designed where the probes end (i.e, at the 3' end) with TCAGCN, where TCAG are matching bases to the target nucleic acid and N is a mismatching base to the target nucleic acid. N can be A, T, G or C; often N is an A or T, sometimes G, and in some embodiments, C.

Studies evaluating double-stranded exonuclease activity (generally described below) have also shown that probes ending with TCAACN or TCACCN work well; and probes ending with TTAGCN or TCAGGN also work relatively well, but not as well as probes ending with TCAGCN.

In additional probe design experiments based on assessing double stranded exonuclease activity, when different template oligos were tested with one probe so that the probe and the template have either 1 or 2 mismatches, such as TCAGCN or TCAGNN (where the N adjacent to the G is a mismatched C residue), the probe and template combination with 2 mismatches resulted in at least 2 fold increase in double-stranded exonuclease activity in comparison to the probe and template combination with 1 mismatch (TCAGCN). Probe and template combinations with 3 mismatches (e.g., TCANNN, where the NN sequence adjacent to the A is a mismatched GC) was similar to probe and template combination with 1 mismatch (TCAGCN) in terms of the double-stranded exonuclease assay. Thus, in some embodiments, probes with two or three mismatches at the 3' end may be desirable. Accordingly, in summary in some embodiments of the invention, it may be desirable to use probes ending with TCAGCN, TCAACN, TCACCN, TTAGCN, TCAGGN or other permutations, where TCAGCN is often preferential to TCAACN or TCACCN, which in turn can be preferential to TTAGCN or TCAGGN. In other embodiments, it may be desirable to employ probes ending with TCAGNN or TCANNN.

Figure 8:
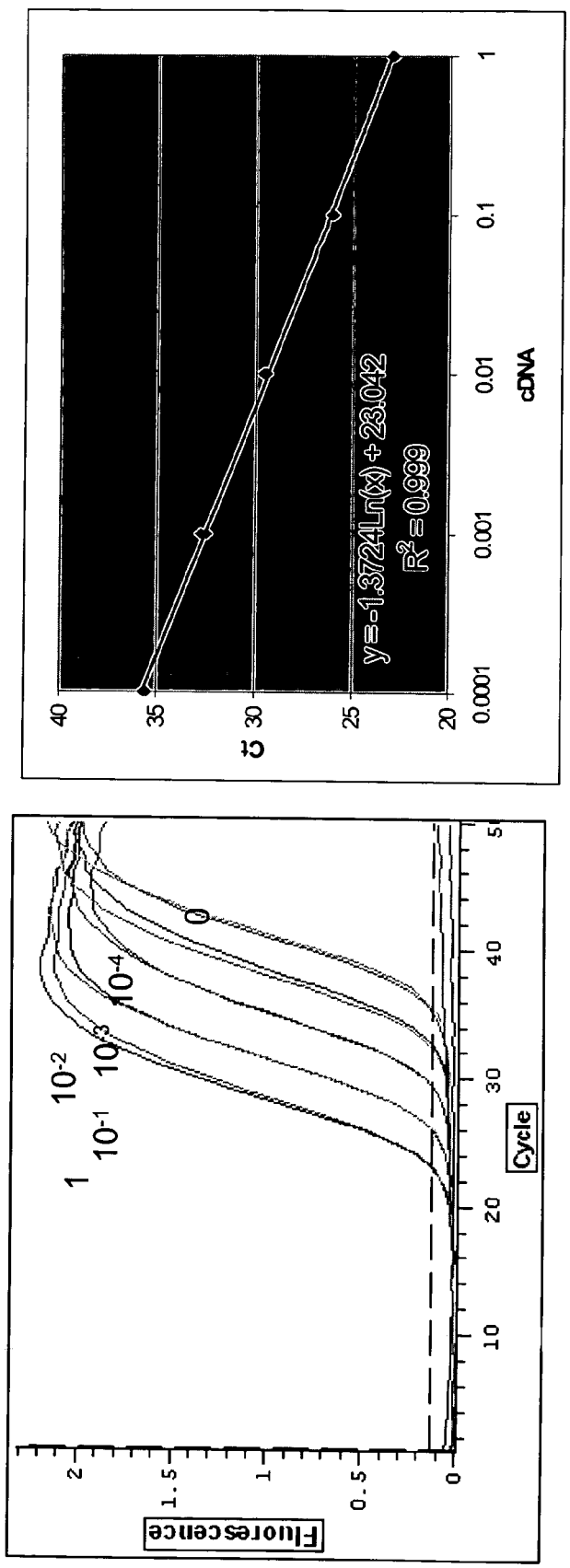
FIG. 8 shows the results of an exemplary qPCR of the invention conducted with one of the probes shown in FIG. 7.

The probes shown in FIG. 7 were evaluated for specificity and sensitivity in quantitative PCR amplifications of the invention (i.e., employing a 3' to 5' nuclease activity). All of the probes provided sensitive, quantitative detection of the target nucleic acid. An example of the results of a qPCR performed to detect human RPLP0 (large ribosomal protein) cDNA is shown in FIG. 8. Serially diluted (10× serial diluted) cDNA derived from human liver total RNA was used as template. The probe employed in the amplification reactions had the sequence FAM-AGAAGGCCTTGAC-CTTTTCAGCT-BHQ1 (SEQ ID NO:8). The reactions were performed using the methodology described in Example 2 Amplification graphs showing detection of the various dilutions of RPLP cDNA is shown in the left panel of FIG. 8. The linear relationship between the Ct values and the log(cDNA amount) values is shown in the right panel of FIG. 8.

Figure 9:
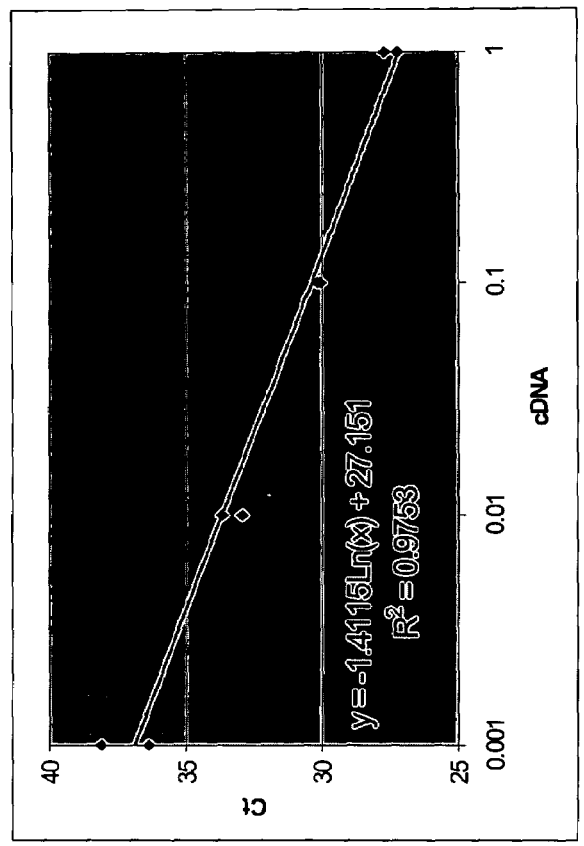
FIG. 9 shows the results of an exemplary qPCR assay using a probe to β2 microglobulin that has a variation of the TCAGC sequence shown in the probes in FIG. 7.
Figure 9:
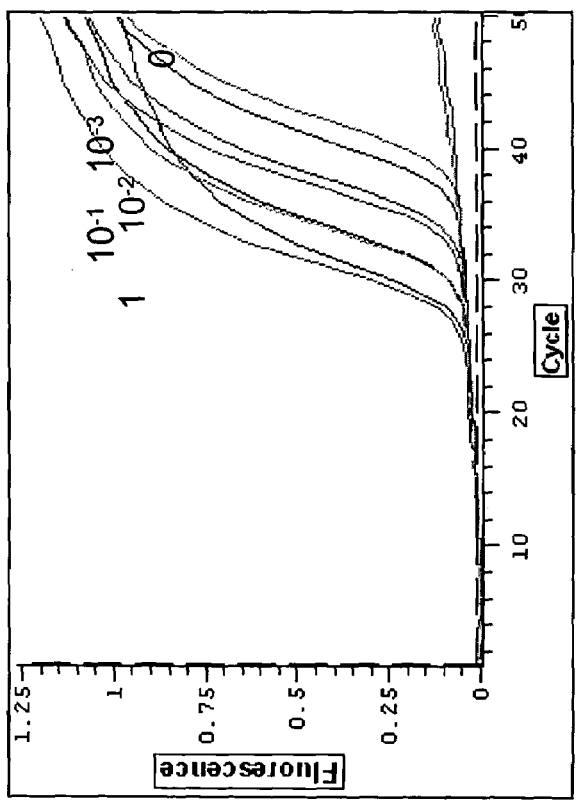

Probes were also tested to demonstrate that the 3' end sequence (TCAGC) described above is not required and that it is not the only nucleotide combination that produces a high signal in this application. A probe to β2-microglobulin (B2M) with a variation of the TCAGC sequence was designed. Results of a qPCR of the invention using the probe are shown in FIG. 9. Ten-fold serially diluted cDNA derived from human liver polyA$^+$ RNA was used as template. The amplification plot is shown in the left panel of FIG. 9. The linear relationship between the Ct values and the log(cDNA amount) values was shown in the right panel of FIG. 9. The B2M probe sequence was FAM-CTTTGGAGTACGCTG-GATAGCCA-BHQ1 (SEQ ID NO:22).

The effect of positioning the 3'-end label on the base or the backbone was also tested. Less sequence dependency by the exonuclease proofreading (exo$^{Pfr}$) activity was found when the 3'-end label was on the base instead of the backbone. However, the probe of this construct became a better substrate for the single-stranded exonuclease (exo$^{ss}$) activity as well (see, e.g., below in Example 4). Of the internally labeled probes that were tested, the highest ratio of exo$^{Pfr}$ to exo$^{ss}$ was found when the mismatch flap was 2 to 4 bases, and the internal label was on the first mismatched base (from the 5'-end).

Probes were also tested that did not include a preferential subsequence. In these experiments, the probes include an abasic site and an internal label (a "T" nucleotide). Examples of such probes that detect particular target sequences that were evaluated are shown in FIG. 10. The probes detect the following target nucleic acids: SDHA: succinate dehydrogenase subunit A; HMBS: hydroxymethyl-bilane synthase; TBP: TATA box-binding protein; UBC: ubiquitin C; RRM: ribonucleotide reductase M1 polypeptide.

Figure 11:
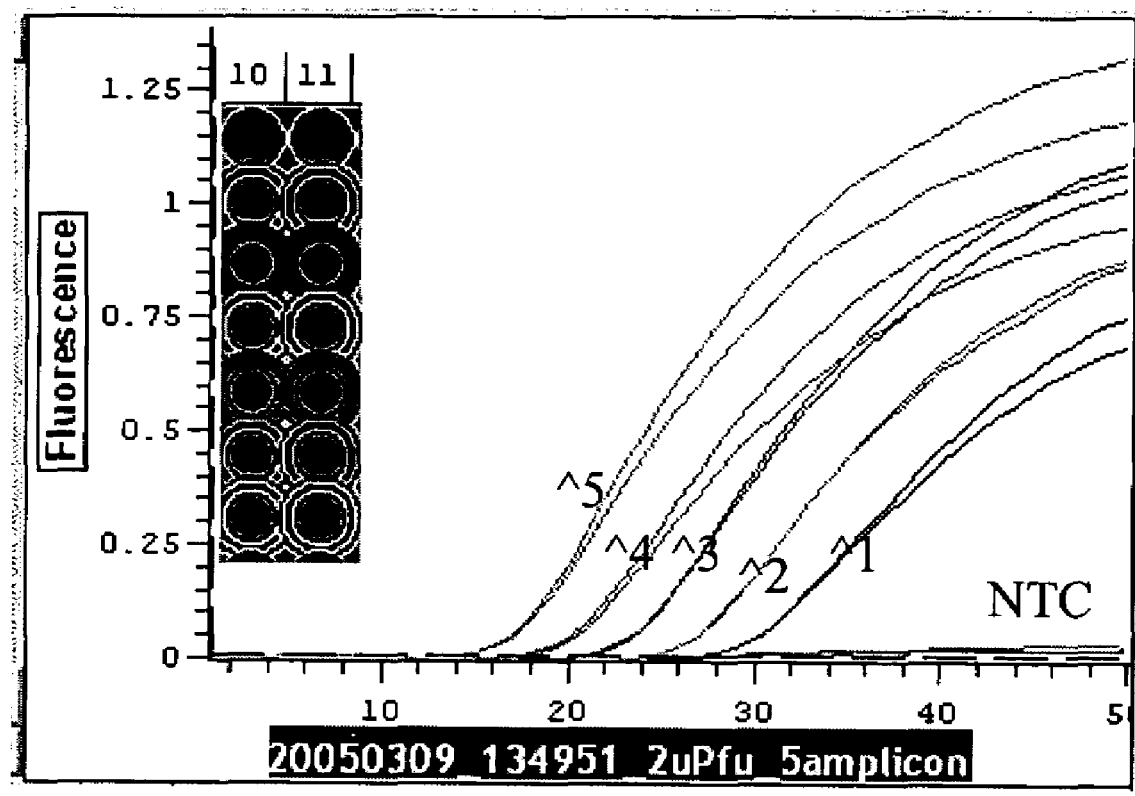
FIG. 11 shows the results of an exemplary qPCR of the invention that specifically detects a uibiquitin sequence using a probe as shown in FIG. 10.

Quantitative amplification reactions employing the probes shown in FIG. 10 were conducted to evaluate sensitivity and specificity. Each probe provided sensitive, specific results. The results of an exemplary assay are shown in FIG. 11. The assay detected 10-fold serial dilutions of a plasmid contain a UBC fragment. The diluted target nucleic acid was amplified in a reaction buffer containing 10 mM Tris pH 8.2, 50 mM KCl, 2.5 mM MgCl2, 0.25 mM each of dNTP, 40 unit/mL of SSt(V), and 25 unit/mL of Pfu. The cycling regimen was: 50 cycles of 15 seconds at 95° C., 30 seconds at 60° C., and 15 seconds at 72° C. Fluorescence was monitored at 60° C. The primers used were UBCFS (5'-ATTTGGGTCGCGGTTCTT*G-3'; SEQ ID NO:23) and UBCRS (5'-TGCCTTGACATTCTCGATGG*T-3'; SEQ ID NO:24), where * stands for a phosphorothiolated bond between the flanking bases. The probe was UBCiFlp4 (5'/ 5IabFQ/GATCTGCATTGTC/idSp/AGTGACGATCA-CAGA/iFluorT/CC-3'; SEQ ID NOS:25 and 26), where /5IabFQ/ is 5' end Iowa Black Quencher FQ, /idSp/ is an internal abasic site, and /iFluorT/ stands for dT with fluorescein attached to the base. The results are shown in FIG. 11. The assay was sensitive and specific and indicates that probes designed to include an abasic site and internally labeled nucleotide also work in this application.

In some embodiments, certain probes are cleaved by the exonuclease activity more efficiently than others. While this in part can relate to the sequence of the probe, different exonuclease activities may also be more efficient than others. In this example, different family B polymerases were evaluated. The results, further described below, showed that different family B polymerases resulted in different $exo^{ds}/exo^{ss}$ ratio with the same probe. In some embodiments, the polymerases that had a higher $exo^{ds}/exo^{ss}$ ratio performed better in qPCR of the invention than the ones with low $exo^{ds}/exo^{ss}$ ratio.

The ratio of $exo^{ds}/exo^{ss}$ was evaluated for various exonucleases. In this analysis, the exonucleases were proteins that are family B polymerases that are deficient in polymerase activity. Two of these proteins (SEQ ID NO:2 and SEQ ID NO:4) and derivative proteins which mutations were introduced into regions predicted to influence exonuclease activity (shown in Table 1) were assayed. The assay for double-stranded substrate activity (DS-Exo assay) was performed in accordance with the following protocol.

Contents of the DS-Exo reaction:
50 mM Tris (pH 8.5)
15 mM $(NH_4)_2SO_4$
2.5 mM $MgCl_2$
5% DMSO
0.3 µM dual labeled probe (GAPD-G: Cy5-5'-CAAGCTTC-CCGTTCTCAGCG-3'-BHQ2; SEQ ID NO:27)
1.2 µM complementary oligo (5'-GCACCGTCAAGCT-GAGAACGGGAAGCTTG-3'; SEQ ID NO:28)
Exonuclease When annealed, the probe and the complementary oligonucleotide form a double stranded DNA as follows. The 3' nucleotide of the probe is mismatched relative to its complementary nucleotide.

Probe (GAPD-G): Cy5-5'-CAAGCTTCCCGTTCT-CAGCG-3'-BHQ2 (SEQ ID NO:27)

Complementary oligo: 3'-GTTCGAAGGGCAAGAGTC-GAACTGCCACG-5' (SEQ ID NO:28)

Figure 12:
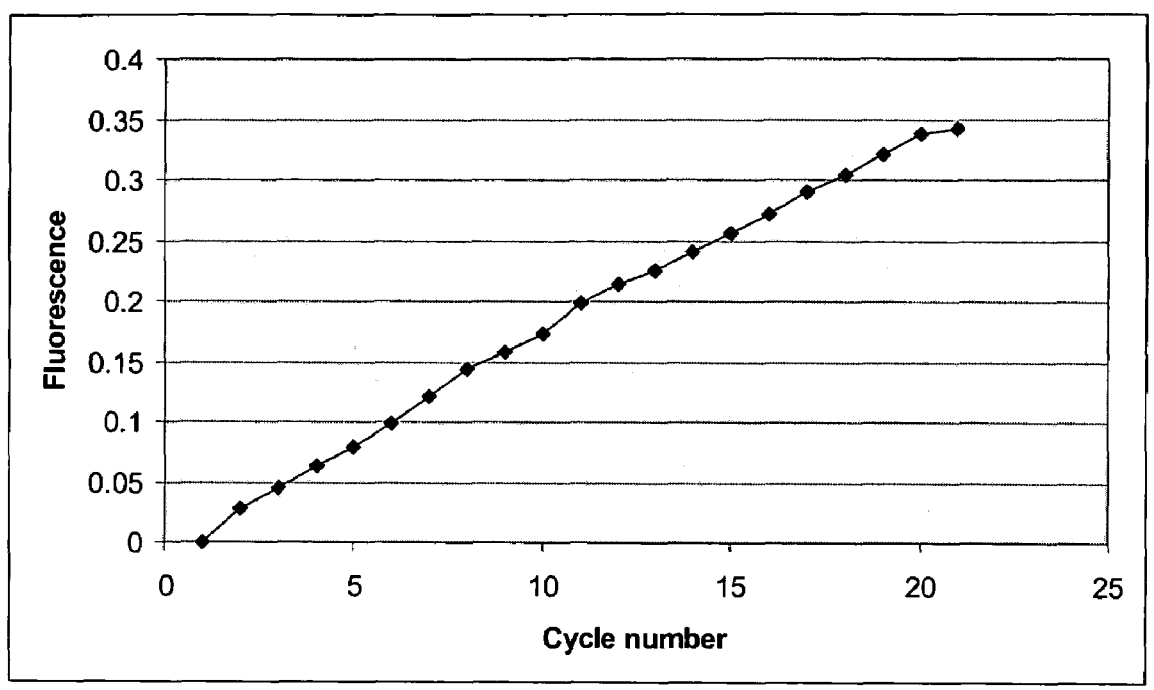
FIG. 12 shows an example of the output of a double-stranded exonuclease activity assessment. The DS-Exo activity is the slope of the line.

The 50 µl reaction was monitored in a Chromo4 Continuous Fluorescence Detector with the following program:
55 degrees 10 seconds
72 degrees 10 seconds
Plate read
Cycle for 20 times FIG. 12 shows an example of the output. The DS-Exo activity is the slope of the line.

The activity of an exonuclease towards a single-stranded substrate (SS-Exo assay) was performed in accordance with the following protocol.

Figure 13:
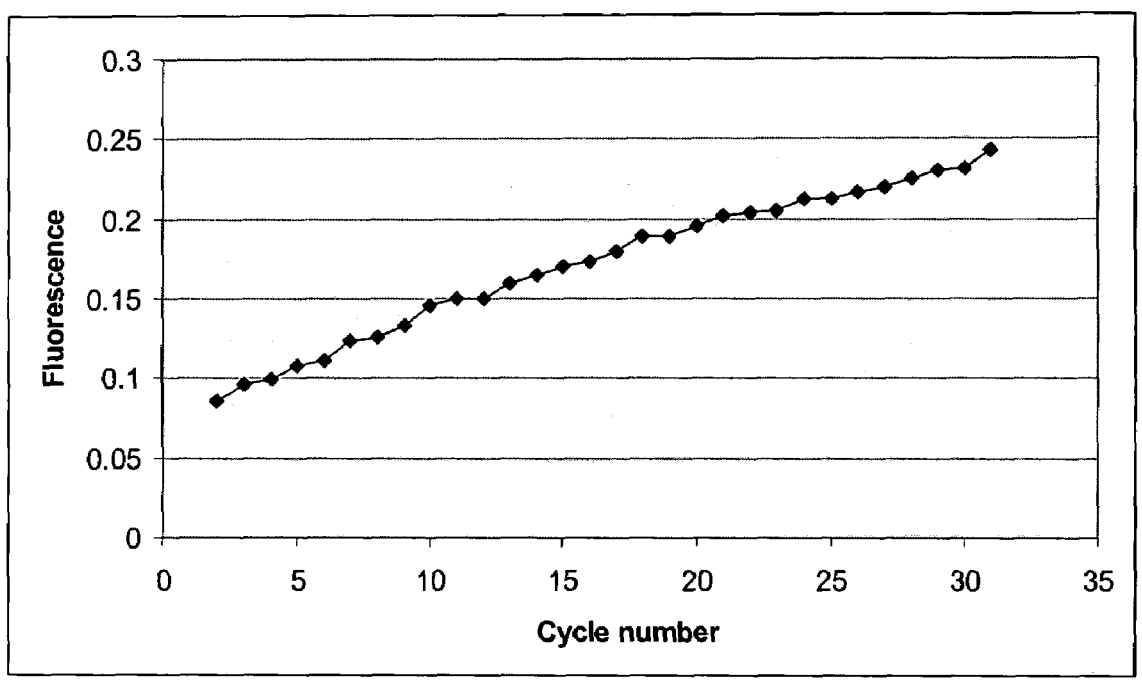
FIG. 13 shows an example of the output of a single-stranded exonuclease activity assessment. The SS-Exo activity is the slope of the line.

Contents of a SS-Exo reaction:
50 mM Tris (pH 8.5)
15 mM $(NH_4)_2SO_4$
2.5 mM $MgCl_2$
5% DMSO
0.3 µM Dual labeled probe (Cy5-5'-CAAGCTTCCCGTTCT-CAGCG-3'-BHQ2; SEQ ID NO:27)
Exonuclease The 50 µl reaction was monitored in a Chromo4 Continuous Fluorescence Detector with the following program:
72 degrees 5 minutes
Plate read
Cycle for 30 times FIG. 13 provides an example of the output. The SS-Exo activity is the slope of the line.

The results (Table 1) showed that three pol⁻exo⁺ proteins that have mutations in the YxGG domain of the protein, A6YX1, A6 YX3, and F11YX2, exhibited significantly higher $exo^{ds}/exo^{ss}$ ratio than the other mutant proteins (A6YX2, F11YX3 and F11SNL1) and the parent proteins.

When the mutant polymerases with the higher $exo^{ds}/exo^{ss}$ ratios were used in qPCRs of the invention, a higher signal level, reflecting the efficiency of the exo enzyme, was obtained for probes that did not work as well with an exo enzyme that contained a wild type YxGG motif and that has a lower $exo^{ds}/exo^{ss}$ ratio. (Summarized in Table 1.)

Polymerase proteins (providing the exonuclease activity) into which mutations in the dNTP binding motif were also evaluated. The dNTP binding motif can be readily ascertained from the structure of the polymerase. In this example, three amino acids, K487, N491, and Y494 were chosen as the targets for site-directed mutagenesis based on the three-dimensional structure of a family B polymerase, with the anticipation that the dNTP binding affinity will be reduced upon the introduction of the mutation(s). F11ΔK and F11ΔY, F11ΔYX2KNY, and F11ΔYX2Y. The $exo^{ds}/exo^{ss}$ ratio assay (Table 1) revealed that all four mutant proteins exhibited significantly higher $exo^{ds}/exo^{ss}$ ratio over that of the proteins that did not contain mutations in the dNTP binding site. Both F11ΔK and F11ΔY showed improved performance in qPCR of the invention compared to the parent counter part. F11ΔYX2KNY and F11ΔYX2Y, which already contained mutations in the YxGG motif, did not show significant further improvement in performance in qPCR. Further more, significant reduction in the background signal due to the cleavage of the probe in the single stranded state was also observed with F11ΔYX2KNY and F11ΔYX2Y, which have the highest $exo_{ds}^{}/exo^{ss}$ ratio, when internally labeled probe with unprotected 3'-terminus was used in a qPCR of the invention.

These results (summarized in Table 1) demonstrated that the $exo^{ds}/exo^{ss}$ ratio can be altered through mutations in the YxGG motif and in the dNTP binding motif. The effect of the two types of mutations was additive.

TABLE 1

Sequence and activity information of the mutant polymerases

| | YxGG motif sequence (385 aa-388 aa in A6 or F11) | SEQ ID NO: | dNTP binding motif mutation | $exo^{ds}/exo^{ss}$ (with GAPD-G probe) | Improves 3' to 5' qPCR performance (relative to wild type control) |
|---|---|---|---|---|---|
| A6YX1 | TTGG | 29 | none | 46 | ++ |
| A6YX2 | DTGG | 30 | none | 59 | + |
| A6YX3 | NTGG | 31 | none | 64 | +++ |
| F11ΔSNL1[a] | NLGG | 32 | none | 57 | + |
| F11ΔYX2 | STGG | 33 | none | 140 | ++/+++ |
| F11ΔYX3 | TAGG | 34 | none | 30 | + |
| A6 or F11Δ | YAGG (wt) | 35 | none | 22[b] (A6) | control |

TABLE 1-continued

Sequence and activity information of the mutant polymerases

| | YxGG motif sequence (385 aa-388 aa in A6 or F11) | SEQ ID NO: | dNTP binding motif mutation | exo$^{ds}$/exo$^{ss}$ (with GAPD-G probe) | Improves 3' to 5' qPCR performance (relative to wild type control) |
|---|---|---|---|---|---|
| F11ΔK | YAGG (wt) | 35 | K487L | 131 | ++ |
| F11ΔY | YAGG (wt) | 35 | Y494A | 289 | ++ |
| F11ΔYX2KNY | DTGG | 30 | K487L/N491A/Y494A | 483 | ++ |
| F11ΔYX2Y | DTGG | 30 | Y494A | 784 | ++ |
| F11Δ | YAGG (wt) | 35 | Wild type | 47 | control |

[a] Δ stands for Sso7d deleted version. In this analysis, the exo enzyme lacking the Sso domain performed better than the ones contain it. A6 naturally lacks the Sso7d domain due to a frame shift mutation at the 3' end of the gene.
[b] A6 and F11Δ were previously shown to exhibit similar exo$^{ds}$/exo$^{ss}$ ratio on the same substrate.

All publications, patents, accession numbers, and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

The nucleic acid and polypeptide sequences of exemplary hybrid polymerase enzymes having exonuclease activity, but that substantially lack polymerase activity are provided below. In SEQ ID NOs:2 and 4, the bolded sequence with the enlarged font shows the positions of the YxGG motif in the sequence.

1. DNA sequence of the gene encoding hybrid enzyme A6 (2274 bp including the stop codon) (SEQ ID NO:1)

```
ATGATCCTGGATGCTGACTACATCACTGAAGACGGCAAACCGATTATCCG
TCTGTTCAAAAAAGAGAACGGCGAATTTAAGGTTGAGTATGATCGCAACT
TTCGTCCATACATTTACGCTCTGCTGAGAGATGATTCTCAGATTGATGAA
GTTAAAAAAATCACTGCTGAGCGCCATGGCAAGATTGTTCGTATCATTGA
TGCGGAAAAGGTAGAAAAGAAATTTCTGGGCAGACCAATCACCGTGTGGA
GACTGTATTTCGAACATCCACAAGATGTTCCGGCTATTCGCGATAAAGTT
CGCGAACATCCTGCAGTTGTTGACATCTTCGAATACGATATTCCATTTGC
AAAGCGTTACCTCATCGACAAAGGCCTGATACCAATGGAGGGCGAGGAAG
AACTCAAGCTCCTGGCGTTCGATATAGAAACCCTCTATCACGAAGGCGAA
GAGTTTGGTAAAGGCCCAATTATAATGATCAGCTATGCAGATGAAAACGA
AGCAAAGGTGATTACTTGGAAAAAAATAGATCTCCCATACGTTGAGGTTG
TATCTTCCGAGCGCGAGATGATTAAGCGCTTTCTCAGAATTATCCGCGAG
AAGGATCCGGACGTTATCGTTACTTATAACGGCGACTCTTTTGACCTCCC
ATATCTGGTGAAACGCGCAGAAAAACTCGGTATTAAACTGCCTCTCGGCC
GTGATGGTTCCGAGCCGAAGATGCAGCGTCTCGGCGATATGACCGCTGTA
GAAGTTAAGGGTCGTATCCATTTCGACCTGTATCATGTAATTACTCGTAC
TATTAACCTCCCGACTTACACTCTCGAGGCTGTATATGAAGCAATTTTTG
GTAAGCCGAAGGAGAAGGTATACGCCCATGAGATTGCAAAGGCGTGGGAA
ACCGGTAAGAACCTCGAGCGTGTTGCAAAATACTCCATGGAAGATGCAAA
GGCGACTTATGAACTCGGCAAAGAATTCTTCCCAATGGAAGCTCAGCTCT
CTCGCCTGGTTGGCCAACCACTGTGGGATGTTTCTCGTTCTTCCACCGGT
AACCTCGTAGAGTGGTTTCTCCTGCGCAAAGCGTACGAACGCAACGAAGT
GGCTCCGAACAAGCCATCTGAAGAAGAGTATGAACGCCGTCTCCGCGAGT
CTTACGCTGGTGGCTTTGTTAAAGAGCCAGAAAAGGGCCTCTGGGAAAAC
CTCGTGTACCTCGATTTTCGCTCTCTGTATCCGTCTATTATCATTACCCA
CAACGTGTCTCCGGATACTCTCAACCGCGAGGGCTGCAGAGAGTATGATG
TTGCTCCGGAAGTAGGCCACAAGTTCTGCAAGGACTTCCCGGGCTTTATT
CCGTCTCTCCTGAAACGTCTGCTCGAGGAACGCCAAGAGATTAAGACTAA
AATGAAGGCGTCCCAGGATCCGATTGAAAAAATAATGCTCGACTATCGCC
AAAGAGCGATTAAAATCCTCGCAAACTCTTATTACGGCTATTATGGCTAT
GCAAAAGCACGCTGGTACTGTAAGGAGTGTGCTGAGTCCGTTACTGCTTG
GGGTCGCGAATACATCGAGCTCGTGCGGAAGGAGCTCGAAGAAAAGTTTG
GCTTTAAAGTTCTCTACATTGACACTGATGGTCTCTATGCGACTATTCCG
GGTGGTGAGCCTGAGGAAATTAAGAAAAAGGCTCTAGAATTTGTGAAATA
CATTAACTCGAAGCTCCCGGGTCTCCTGGAGCTCGAATATGAAGGCTTTT
ATGTTCGCGGCTTCTTCGTTACCAAGAAGAGATATGCGGTGATTGATGAA
GAAGGCAAAATTATTACTCGTGGTCTCGAGATTGTGCGCCGTGATTGGAG
CGAAATTGCGAAAGAAACTCAAGCTAGAGTTCTCGAGGCTATTCTCAAAC
ACGGCAACGTTGAAGAAGCTGTGAAAATTGTAAAAGAAGTAACCCAAAAG
CTCGCTAAATATGAAATTCCGCCAGAGAAGCTCGCGATTTATGAGCAGAT
TACTCGCCCGCTGCATGAGTATAAGGCGATTGGTCCGCACGTGGCTGTTG
CAAAGAGACTGGCTGCTAGAGGCGTGAAAGTTAGACGGGTATGGTAATT
GGCTACATTGTACTCCGCGGCGATGGTCCGATTAGCAACCGTGCAATTCT
AGCTGAGGAATACGATCTGAAAAAGCACAAGTATGACGCAGAATATTACA
```

```
TTGAGAACCAGGTGCTCCCGGCGGTACTCCGTATTCTGGAGGCTTTTGGC
TACCGTAAGGAAGACCTCCGCTGA
```

2. Amino acid sequence (757 aa) of hybrid enzyme A6 (SEQ ID NO:2)

```
MILDADYITEDGKPIIRLFKKENGEFKVEYDRNFRPYIYALLRDDSQIDE
VKKITAERHGKIVRIIDAEKVEKKFLGRPITVWRLYFEHPQDVPAIRDKV
REHPAVVDIFEYDIPFAKRYLIDKGLIPMEGEEELKLLAFDIETLYHEGE
EFGKGPIIMISYADENEAKVITWKKIDLPYVEVVSSEREMIKRFLRIIRE
KDPDVIVTYNGDSFDLPYLVKRAEKLGIKLPLGRDGSEPKMQRLGDMTAV
EVKGRIHFDLYHVITRTINLPTYTLEAVYEAIFGKPKEKVYAHEIAKAWE
TGKNLERVAKYSMEDAKATYELGKEFFPMEAQLSRLVGQPLWDVSRSSTG
NLVEWFLLRKAYERNEVAPNKPSEEEYERRLRESYAGGFVKEPEKGLWEN
LVYLDFRSLYPSIIITHNVSPDTLNREGCREYDVAPEVGHKFCKDFPGFI
PSLLKRLLEERQEIKTKMKASQDPIEKIMLDYRQRAIKILANSYYGYYGY
AKARWYCKECAESVTAWGREYIELVRKELEEKFGFKVLYIDTDGLYATIP
GGEPEEIKKKALEFVKYINSKLPGLLELEYEGFYVRGFFVTKKRYAVIDE
EGKIITRGLEIVRRDWSEIAKETQARVLEAILKHGNVEEAVKIVKEVTQK
LAKYEIPPEKLAIYEQITRPLHEYKAIGPHVAVAKRLAARGVKVRPGMVI
GYIVLRGDGPISNRAILAEEYDLKKHKYDAEYYIENQVLPAVLRILEAFG
YRKEDLR*
```

3. DNA sequence of the gene encoding hybrid enzyme F11 (2535 bp including the stop) (SEQ ID NO:3)

```
ATGATCCTGGATGCTGACTACATCACTGAAGACGGCAAACCGATTATCCG
TCTGTTCAAAAAAGAGAACGGCGAATTTAAGGTTGAGTATGATCGCAACT
TTCGTCCATACATTTACGCTCTGCTGAGAGATGATTCTCAGATTGATGAA
GTTAAAAAAATCACTGCTGAGCGCCATGGCAAGATTGTTCGTATCATTGA
TGCGGAAAAGGTAGAAAAGAAATTTCTGGGCAGACCAATCACCGTGTGGA
GACTGTATTTCGAACATCCACAAGATGTTCCGGCTATTCGCGATAAAGTT
CGCGAACATCCTGCAGTTGTTGACATCTTCGAATACGATATTCCATTTGC
AAAGCGTTACCTCATCGACAAAGGCCTGATACCAATGGAGGGCGAGGAAG
AACTCAAGCTCCTGGCGTTCGATATAGAAACCCTCTATCACGAAGGCGAA
GAGTTTGGTAAAGGCCCAATTATAATGATCAGCTATGCAGATGAAAACGA
AGCAAAGGTGATTACTTGGAAAAAAATAGATCTCCCATACGTTGAGGTTG
TATCTTCCGAGCGCGAGATGATTAAGCGCTTTCTCAAAATTATCCGCGAG
AAGGATCCGGACGTTATCGTTACTTATAACGGCGACTCTTTTGACTTCCC
ATATCTGGTGAAACGCGCAGAAAAACTCGGTATTAAACTGACTATCGGCC
GTGATGGTTCCGAGCCGAAGATGCAGCGTCTCGGCGATATGACCGCTGTA
GAAATTAAGGGTCGTATCCATTTCGACCTGTATCATGTAATTCGTCGTAC
TATTAACCTCCCGACTTACACTCTCGAGGCTGTATATGAAGCAATTTTTG
GTAAGCCGAAGGAGAAGGTATACGCCGATGAGATTGCAGAGGCGTGGGAA
TCCGGTGAGGGCCTCGAGCGTGTTGCAAAATACTCCATGGAAGATGCAAA
GGTGACTTATGAACTCGGCAAAGAATTCCTCCCAATGGAAATCCAGCTCT
CTCGCCTGGTTGGCCAACCACTGTGGGATGTTTCTCGTTCTTCCACCGGT
AACCTCGTAGAGTGGTTTCTCCTGCGCAAAGCGTACGAACGCAACGAAGT
GGCTCCGAACAAGCCATCTGAAGAAGAGTATGAACGCCGTCTCCGCGAGT
CTTACGCTGGTGGCTATGTTAAAGAGCCAGAAAAGGGCCTCGGGAAAAAC
CTCGTGTACCTCGATTTTCGCTCTCTGGATCCGACATTATCATTACCCA
CAACGTGTCTCCGGATACTCTCAACCGCGAGGGCTGCAGAGAGTATGATG
TTGCTCCGGAAGTAGGCCACAAGTTCTGCAAGGACTTCCCGGGCTTTATT
CCGTCTCTCCTGAAACGTCTGCTCGAGGAACGCCAAGAGATTAAGACTAA
AATGAAGGCGTCCCAGGATCCGATTGAAAAAATAATGCTCGACTATCGCC
AAAGAGCGATTAAAATCCTCGCAAACTCTTATTACGGCTATTATGGCTAT
GCAAAAGCACGCTGGTACTGTAAGGAGTGTGCTGAGTCCGTTACTGCTTG
GGGTCGCGAATACATCGAGCTCGTGCGGAAGGAGCTCGAAGAAAAGTTTG
GCTTTAAAGTTCTCTACATTGACACTGATGGTCTCTATGCGACTATTCCG
GGTGGTGAGCCTGAGGAAATTAAGAAAAAGGCTCTAGAATTTGTGAAATA
CATTAACTCGAGCTCCCGGGTCTCCTGGAGCTCGAATATGAAGGCTTTTA
TGTTCGCGGCTTCTTCGTTACCAAGAAGAGATATGCGCTGATTGATGAAG
AAGGCAAAATTATTACTCGTGGTCTCGAGATTGTGCGCCGTGATTGGAGC
GAAATTGCGAAAGAAACTCAAGCTAGAGTTCTCGAGACTATTCTCAAACA
CGGCAACGTTGAAGAAGCTGTGAGAATTGTAAAAGAAGTAACCAAAAAGC
TCTCTAACTATGAAATTCCGCCAGAGAAGCTCGCGATTTATGAGCAGATT
ACTCGCCCGCTGCATGAGTATAAGGCGATTGGTCCGCACGTGGCTGTTGC
AAAGAGACTGGCTGCTAAAGGCGTGAAAATTAGACCGGGTATGGTAATTG
GCTACATTGTACTCCGCGGCGATGGTCCGATTAGCAACCGTGCAATTCTA
GCTGAGGAATACGATCCGAAAAAGCACAAGTATGACGCAGAATATTACAT
TGAGAACCAGGTGCTCCCGGCGGTACTCCGTATTCTGGAGGCTTTTGGCT
ACCGTAAGGAAGACCTCCGCTGCCAAAAGACTAAACAGACTGGCCTCACT
GCTTGGCTCAACATTAAAAAATCCGGTACCGGCGGTGGCGGTGCAACCGT
AAAGTTCAAGTACAAAGGCGAAGAAAAGAGGTAGACATCTCCAAGATCA
AGAAAGTATGGCGTGTGGGCAAGATGATCTCCTTCACCTACGACGAGGC
GGTGGCAAGACCGGCCGTGGTGCGGTAAGCGAAAAGGACGCGCCGAAGGA
GCTGCTGCAGATGCTGGAGAAGCAGAAAAAGTGA
```

4. Amino acid sequence (844 aa) of hybrid-enzyme F11 (SEQ ID NO:4)

```
MILDADYITEDGKPIIRLFKKENGEFKVEYDRNFRPYIYALLRDDSQIDE
VKKITAERHGKIVRIIDAEKVEKKFLGRPITVWRLYFEHPQDVPAIRDKV
REHPAVVDIFEYDIPFAKRYLIDKGLIPMEGEEELKLLAFDIETLYHEGE
```

-continued

EFGKGPIIMISYADENEAKVITWKKIDLPYVEVVSSEREMIKRFLKIIRE
KDPDVIVTYNGDSFDFPYLVKRAEKLGIKLTIGRDGSEPKMQRLGDMTAV
EIKGRIHFDLYHVIRRTINLPTYTLEAVYEAIFGKPKEKVYADEIAEAWE
SGEGLERVAKYSMEDAKVTYELGKEFLPMEIQLSRLVGQPLWDVSRSSTG
NLVEWFLLRKAYERNEVAPNKPSEEEYERRLRESYAGGYVKEPEKGLWEN
LVYLDFRSLDPDIIITHNVSPDTLNREGCREYDVAPEVGHKFCKDFPGFI
PSLLKRLLEERQEIKTKMKASQDPIEKIMLDYRQRAIKILANSYYGYYGY

-continued

AKARWYCKECAESVTAWGREYIELVRKELEEKFGFKVLYIDTDGLYATIP
GGEPEEIKKKALEFVKYINSKLPGLLELEYEGFYVRGFFVTKKRYALIDE
EGKIITRGLEIVRRDWSEIAKETQARVLETILKHGNVEEAVRIVKEVTKK
LSNYEIPPEKLAIYEQITRPLHEYKAIGPHVAVAKRLAAKGVKIRPGMVI
GYIVLRGDGPISNRAILAEEYDPKKHKYDAEYYIENQVLPAVLRILEAFG
YRKEDLRCQKTKQTGLTAWLNIKKSGTGGGGATVKFKYKGEEKEVDISKI
KKVWRVGKMISFTYDEGGGKTGRGAVSEKDAPKELLQMLEKQKK*

What is claimed is:

1. A method of quantifying a target nucleic acid in an amplification reaction, the method comprising
    incubating an amplification reaction that comprises a template comprising the target nucleic acid with:
        amplification primers,
        a polymerase,
        an enzyme having 3' to 5' exonuclease activity, and
        a probe in which the 3' end of the probe has the sequence TCAGCN, TCAGCTN, or TCANNN, wherein each of the N residues represents a mismatch to the target nucleic acid sequence,
    where the amplification reaction is incubated under conditions in which
        i) the amplification primers are extended by the polymerase to amplify the target nucleic acid;

ii) the probe specifically hybridizes to the target nucleic acid, wherein the 3' nucleotide is cleaved from the probe; and detecting the amount of cleavage product, thereby quantifying the target nucleic acid.

2. The method of claim 1, wherein two or more of the 3' nucleotides of the probes are mismatched.

3. The method of claim 1, wherein the probe has the sequence TCAGCN at the 3' end.

4. The method claim 1, wherein the step of detecting the amount of cleaved 3' nucleotide comprises determining the Ct.

5. The method of claim 1, wherein is the enzyme having 3' to 5' exonuclease activity and the polymerase are the same polypeptide.

6. The method of claim 1, wherein the 3' to 5' exonuclease activity is provided a proofreading polymerase.

7. The method of claim 1, wherein the enzyme having 3' to 5' exonuclease activity and the polymerase are different polypeptides.

8. The method of claim 7, wherein the 3' to 5' exonuclease activity is provided by a mutant error-correcting polymerase that lacks substantial polymerase activity.

9. The method of claim 1, wherein the polymerase comprises a sequence nonspecific double stranded nucleic acid binding domain.

10. The method of claim 9, wherein the sequence nonspecific double stranded nucleic acid binding domain is an Sso7 domain selected from the group consisting of a Sso7d domain, a Sac7d domain, and a Sac7e domain.

11. The method of claim 1, wherein the polymerase is a family A polymerase.

12. The method of claim 11, wherein the polymerase lacks 5' to 3' exonuclease activity.

13. The method of claim 11, wherein the polymerase is Klenow fragment.

14. The method of claim 11, wherein the family A polymerase is thermostable.

15. The method of claim 14, wherein the family A polymerase is from *Carboxydothermus hydrogenoformans*.

16. The method of claim 1, wherein the polymerase is a family B polymerase.

17. The method of claim 16, wherein the family B polymerase is thermostable.

18. The method of claim 17, wherein the family B polymerase is a *Pryococcus* polymerase.

19. The method of claim 18, wherein the polymerase is a *Pyrococcus furiosus* (Pfu) polymerase.

20. The method of claim 1, wherein the polymerase is a hybrid polymerase.

21. The method of claim 1, wherein the polymerase is a hot-start polymerase.

22. The method of claim 1, wherein the probe comprises an abasic site at an internal position of the probe.

23. The method of claim 1, wherein the probe is labeled with a detectable moiety at an internal nucleotide.

24. The method of claim 23, wherein the internal nucleotide having the detectable label is within 10 nucletides of the 3' end of the probe.

25. The method of claim 23, wherein the probe comprises an abasic site at an internal position of the probe.

26. The method of claim 1, wherein the probe is labeled with a detectable moiety at the 3' end.

27. The method of claim 1, wherein the probe is double-labeled with two interacting moieties, wherein one of the interacting moieties is on the 3' end.

28. The method of claim 27, wherein the cleaved 3' nucleotide is detected by detecting a change in fluorescence intensity.

29. The method of claim 27, wherein the moiety on the 3' nucleotide is a quencher and the second interacting moiety is a fluorescent label.

30. The method of claim 27, wherein the moiety on the 3' end is a fluorescent label and the second interacting moiety is a quencher.

31. The method of claim 27, wherein the moiety on the 3' end is a fluorescent label and the second interacting moiety is second fluorescent label.

32. The method claim 1, wherein the 3' end is labeled with a fluorescent label and cleavage of the 3' nucleotide is detected by a change in fluorescent polarization.

33. The method claim 1, wherein one or more of the cleaved products is detected by mass spectroscopy.

34. The method of claim 1, wherein the probe further comprises at least one phosphorothioate linkages.

35. The method of claim 34, wherein the phosphorothioate linkage is between the 3' nucleotide of the probe and the adjacent nucleotide.

36. The method of claim 1, wherein the probe comprises a minor groove binding moiety.

37. The method of claim 1, wherein the minor groove binding moiety is at the 5' end of the probe.

38. The method of claim 1, wherein the reaction is a multiplex reaction.

39. The method of claim 1, wherein the probe has a TCANNN at the 3' end.

40. The method of claim 39, wherein the probe ends in TCAGCN, TCAACN, TCACCN, TCAGNN, or TCAGGN.

41. The method of claim 1, wherein the probe has a sequence TCAGCTN at the 3' end.

* * * * *